US012710421B2

(12) United States Patent
Shenhar-Tsarfaty et al.

(10) Patent No.: US 12,710,421 B2
(45) Date of Patent: Aug. 18, 2026

(54) NON-INVASIVE ASSAY FOR DIFFERENTIATING BETWEEN BACTERIAL AND VIRAL INFECTIONS

(71) Applicants: ICHILOV TECH LTD., Tel Aviv (IL); YEDA RESEARCH AND DEVELOPMENT CO. LTD., Rehovot (IL)

(72) Inventors: Shani Shenhar-Tsarfaty, Kibbutz Gesher (IL); Shlomo Avraham Berliner, Givataim (IL); Ori Rogowski, Tel Aviv (IL); Eyal Fisher, Hod Hasharon (IL); Adi Silberman, Tel Aviv (IL)

(73) Assignees: ICHILOV TECH LTD., Tel Aviv (IL); YEDA RESEARCH AND DEVELOPMENT CO. LTD., Rehovot (IL)

( * ) Notice: Subject to any disclaimer, the term of this patent is extended or adjusted under 35 U.S.C. 154(b) by 952 days.

(21) Appl. No.: 17/781,704

(22) PCT Filed: Dec. 10, 2020

(86) PCT No.: PCT/IL2020/051277

§ 371 (c)(1),
(2) Date: Jun. 1, 2022

(87) PCT Pub. No.: WO2021/117044

PCT Pub. Date: Jun. 17, 2021

(65) Prior Publication Data

US 2023/0016954 A1 Jan. 19, 2023

Related U.S. Application Data

(60) Provisional application No. 62/946,437, filed on Dec. 11, 2019.

(51) Int. Cl.
*G01N 33/569* (2006.01)

(52) U.S. Cl.
CPC . *G01N 33/56911* (2013.01); *G01N 33/56983* (2013.01)

(58) Field of Classification Search
CPC .................. G01N 33/56911; G01N 33/56983
See application file for complete search history.

(56) References Cited

U.S. PATENT DOCUMENTS

| | | | |
|---|---|---|---|
| 4,313,734 | A | 2/1982 | Leuvering |
| 4,376,110 | A | 3/1983 | David et al. |
| 4,632,901 | A | 12/1986 | Valkirs |
| 4,786,589 | A | 11/1988 | Rounds |
| 4,816,567 | A | 3/1989 | Cabilly et al. |
| 5,189,178 | A | 2/1993 | Galardy et al. |
| 5,239,078 | A | 8/1993 | Galardy et al. |
| 5,656,448 | A | 8/1997 | Kang |
| 9,200,324 | B2 | 12/2015 | Cavet et al. |
| 9,726,668 | B2 | 8/2017 | Oved |
| 2003/0036070 | A1 | 2/2003 | Chakravati |
| 2009/0280108 | A1 | 11/2009 | Gong et al. |
| 2011/0137851 | A1 | 6/2011 | Cavet et al. |
| 2013/0034868 | A1 | 2/2013 | Liao |
| 2013/0122528 | A1* | 5/2013 | Tyrell ................ G01N 33/6893 435/7.92 |
| 2015/0038595 | A1 | 2/2015 | Anderberg |
| 2015/0045245 | A1 | 2/2015 | Vanpoucke et al. |
| 2015/0203899 | A1 | 7/2015 | Levin |
| 2017/0114392 | A1* | 4/2017 | Sambursky ...... G01N 33/56911 |
| 2017/0269081 | A1 | 9/2017 | Oved |
| 2019/0011456 | A1* | 1/2019 | Oved ................ G01N 33/6863 |
| 2019/0144943 | A1 | 5/2019 | Khatri |
| 2019/0323065 | A1 | 10/2019 | Levin |
| 2020/0255898 | A1 | 8/2020 | Deirmengian |

FOREIGN PATENT DOCUMENTS

| | | | | |
|---|---|---|---|---|
| EP | 0125118 | B1 | 9/1992 | |
| EP | 2711710 | B1 | 4/2017 | |
| KR | 100925147 | | 11/2009 | |
| WO | 2004059293 | A2 | 7/2004 | |
| WO | 2006063213 | | 6/2006 | |
| WO | 2013075055 | | 5/2013 | |
| WO | 2013083781 | | 6/2013 | |
| WO | 2014117746 | | 8/2014 | |
| WO | 2016079219 | A1 | 5/2016 | |
| WO | 2016081941 | A1 | 5/2016 | |
| WO | WO-2018035563 | A1 * | 3/2018 | ............ C12Q 1/701 |
| WO | 2018114044 | | 6/2018 | |

(Continued)

OTHER PUBLICATIONS

Lamps LW. "Beyond acute inflammation: a review of appendicitis and infections of the appendix", Diagnostic Histopathology, vol. 4, Issue 2, pp. 68-77 (Year: 2008).*

Gannon et al (2019) A point-of-care assay for alpha-1-acid glycopene as a diagnostic tool for rapid mobile-based determination of inflammation, Curr Res Biotechnol 1: 41-48.

Jain, KK (2019) Biomarkers of Infectious Diseases, in the Handbook of Biomarkers, Humana Press, NY, NY pp. 219-238.

Merryfield 1963) Solid Phase Peptide Synthesis I, The synthesis of a Tetrapeptide, J Am Chem Soc, 85(14): 2149-2154.

Oveland et al (2012) Proteomic evaluation of inflammatory proteins in a rat spleen interstitial fluid and lymph during LPS-induced systemic inflammation reveals increased levels of ADAMST1, J Proteome Res, 11(11): 5338-5349.

(Continued)

*Primary Examiner* — Peter Johansen
(74) *Attorney, Agent, or Firm* — Greenberg Traurig LLP

(57) ABSTRACT

The invention provides assays and methods for diagnosing and treating infectious diseases. The invention relates in some embodiments to urinary biomarkers and their use in the differential diagnosis of bacterial and viral infections. The invention further relates to means for determining and providing correct treatment to infection in a non-invasive manner, while minimizing antibiotic misuse.

10 Claims, 3 Drawing Sheets

(56) References Cited

FOREIGN PATENT DOCUMENTS

WO 2019027910 2/2019

OTHER PUBLICATIONS

Prasad et al (2016) Detection of inflammatory biomarkers in saliva and urine: Potential in diagnosis, prevention and treatment for chronic diseases, Experimental Biology and Medicine, 241:793-799.

Yamada, Toshiyuki (1999) Serum Amyloid A (SAA): A Concise Review of Biology, Assay Methods and Clinical Usefulness, Clin Chem Lab Meth 37(4):381-388.

McCormack et al (1996) Generation of soluble recombinant human acute phase serum amyloid A2 (A-SAA2) protein and its use in development of a A-SAA specific ELISA, Journal of Immunological Methods, vol. 198:101-110.

Bioulac-Sage et al (2007) Hepatocellular Adenoma Subtype Classification Using Molecular Markers and Immunochemistry, Hepatology 46(3):704-748.

Cdi Laboratories: HuProt™ Human Proteome Microarray v4.0 (2019) [https://cdi.bio/wp-content/uploads/2019/11/CDI_HuProt_v4.0_Manual_6-19.pdf].

Ashkenazi-Hoffnung et al., (2018) A host-protein signature is superior to other biomarkers for differentiating between bacterial and viral disease in patients with respiratory infection and fever without source: a prospective observational study. Eur J Clin Microbiol Infect Dis 37(7): 1361-1371.

Denz et al., (1990) Value of urinary neopterin in the differential diagnosis of bacterial and viral infections. Klin Wochenschr 68(4): 218-222.

Jortani et al., (2004) Sensitive noninvasive marker for the diagnosis of probable bacterial or viral infection. J Clin Lab Anal 18(6): 289-295.

Lydon et al., (2019) Validation of a host response test to distinguish bacterial and viral respiratory infection. EBioMedicine 48: 453-461.

Oved et al., (2015) A novel host-proteome signature for distinguishing between acute bacterial and viral infections. PLoS One 10(3): e0120012.

Reisinger et al., (2014) Non-invasive serum amyloid A (SAA) measurement and plasma platelets for accurate prediction of surgical intervention in severe necrotizing enterocolitis (NEC). PLoS One 9(6): e90834.

Rodríguez-Ortiz et al., (2018) Novel Urinary Biomarkers for Improved Prediction of Progressive Egfr Loss in Early Chronic Kidney Disease Stages and in High Risk Individuals Without Chronic Kidney Disease. Sci Rep 8(1): 15940 with erratum.

Sweeney et al., (2016) Robust classification of bacterial and viral infections via integrated host gene expression diagnostics. Sci Transl Med. Author manuscript; available in PMC Mar. 14, 2017. Published in final edited form as: Sci Transl Med. Jul. 6, 2016; 8(346): 346ra91.

Valim et al., (2016) Responses to Bacteria, Virus, and Malaria Distinguish the Etiology of Pediatric Clinical Pneumonia. Am J Respir Crit Care Med 193(4): 448-459.

Whetton et al., (2020) Proteomics and Informatics for Understanding Phases and Identifying Biomarkers in COVID-19 Disease. J. Proteome Res 19(11): 4219-4232.

* cited by examiner

NON-INVASIVE ASSAY FOR DIFFERENTIATING BETWEEN BACTERIAL AND VIRAL INFECTIONS

CROSS-REFERENCE TO RELATED APPLICATIONS

This application is the U.S. National Stage of International Patent Application No. PCT/IL2020/051277, filed on Dec. 10, 2020, which claims the benefit of and priority to U.S. Provisional Patent Application No. 62/946,437, filed on Dec. 11, 2019, the contents of each of which are hereby incorporated by reference in their entireties.

FIELD OF THE INVENTION

The invention provides assays and methods for diagnosing and treating infectious diseases. Particularly, the invention relates to the use of urinary biomarkers for providing differential diagnosis of bacterial and viral infections.

BACKGROUND OF THE INVENTION

Resistant bacteria have become one of the greatest threats to global health. The antibiotic resistance crisis has been attributed to the overuse and misuse of antibiotics, as well as a lack of new drug development by the pharmaceutical industry. A major reason for the overuse and misuse of antibiotics is incorrect diagnosis, stemming from the difficulty of distinguishing between certain infection etiologies. In particular, bacterial and viral infections are often clinically indistinguishable, leading to inappropriate patient management and antibiotic misuse.

Treating viral infections or inflammation of non-infectious etiologies with antibiotics is ineffective, may cause toxic or allergic reactions, and importantly, contributes to the development of resistant bacteria. Yet, in a case that there is a doubt whether an infection is bacterial or viral in origin, clinicians often prescribe unnecessary antibiotics to eliminate the risk of developing a life-threatening bacterial infection associated with sepsis and organ failure. The rate of inappropriate antibiotic prescriptions in the hospital setting is estimated at 30 to 50%. Improved diagnostics for acute infections could decrease morbidity and mortality by increasing early antibiotics for patients with bacterial infections and reducing unnecessary antibiotics for patients without bacterial infections.

Currently, there is no gold standard point-of-care diagnostic method that can discriminate between bacterial and viral infections, but routinely used microbiological diagnostic tests such as culture, serology and more recently nucleic acid-based tests can assist the clinician in the etiological determination of the underlying infectious process. The challenges for accurate diagnosis of infections include pathogen detection in cases that the infection site is not readily accessible or unknown, long time of microbiological laboratory assays, understanding whether a detected bacterium is the disease-causing agent or a mere colonizer, and mixed infection with both viruses and bacteria.

The biological response of body tissues to injury, infection or irritation is typically characterized by inflammation, an innate immune reaction in which a cascade of cellular and microvascular events serves to eradicate the infection, remove damaged tissue and generate new tissue. During this process, elevated permeability in microvessels allows neutrophils and mononuclear cells to leave the intravascular compartment, and perform various anti-microbial activities to eradicate the injury.

Sepsis is a clinical syndrome that complicates severe infection, which is characterized by a dysregulated, systemic inflammation, and may progress to increasingly severe tissue injury, organ failure and death. Septic shock is a severe form of sepsis, with significantly increased mortality due to increased abnormalities of circulation and/or cellular metabolism. Early recognition and treatment of sepsis is key to improved survival, as the source of infection, which is most often bacterial, should be controlled as early as possible. However, systemic inflammation and manifestation of signs and symptoms associated with sepsis may also occur in the absent of infection, for example as a result of ischemia, trauma or malignancy.

The concept of the systemic inflammatory response syndrome (SIRS), defined by certain abnormalities of vital signs and laboratory results, has been introduced in 1992, to define a clinical response to a non-specific insult, wherein SIRS accompanied by a documented or presumed infection has been defined as sepsis. However, SIRS criteria have been found to lack sensitivity and specificity for increased mortality risk, which is the main consideration for using such a conceptual model. Blood levels of certain cytokines and acute phase proteins, such as C-reactive protein (CRP), are also used to evaluate the level of systemic inflammation, thereby assisting in the evaluation of infectious and non-infectious inflammatory conditions.

Recently, models of host-based peripheral blood gene expression analysis have been suggested to assist in diagnosis of infectious diseases. However, translation into clinical practice remains elusive. Most of the models were not tested in multiple independent cohorts, had too many genes to allow rapid profiling necessary for useful diagnosis, or both.

Sweeney T. E., et al. (Sci Transl Med. 2016; 8.346: 346ra91) used multicohort analysis of gene expression in blood to derive a set of seven markers for discrimination of bacterial and viral infections.

To improve the performance of individual host-proteins, combinations of several proteins into a single predictive score have been proposed (E. G. Oved, K., et al. PLoS One 2015; 10.3; Valim, C., et al. Am. J. Respir. Crit. Care Med. 2016; 193:448-459). However, in most studies the suggested combinations provided only limited-to-moderate diagnostic improvement over individual proteins, and/or exhibited other drawbacks such as limited discriminative power when considering multiple patient categories.

U.S. Pat. No. 9,726,668 discloses signatures and determinants for diagnosing infections and methods of use thereof. Some aspects provide methods using biomarkers for rapidly detecting the source of infection and administrating the appropriate treatment.

WO 2018/035563 relates to compositions, methods and apparatus for diagnosing and/or monitoring an infection by a bacterium, virus or protozoan by measurement of pathogen-associated and non-infectious systemic inflammation and optionally in combination with detection of a pathogen specific molecule. More particularly, WO '563 discloses host peripheral blood RNA and protein biomarkers, which are used in combination, and optionally with peripheral blood broad-range pathogen-specific detection assays.

US 2019/144943 discloses methods for diagnosis of bacterial and viral infections, in particular to the use of biomarkers that can determine whether a patient with acute inflammation has a bacterial or viral infection. More specifically, the combined use of multiple biomarker lists is contemplated, including a list of polynucleotides comprising nucleotide sequences from genes or RNA transcripts of genes that are differentially expressed in patients having a viral infection compared to control subjects, differentially expressed in patients having a bacterial infection compared to control subjects, or differentially expressed in patients having sepsis or an infection compared to control subjects.

Ashkenazi-Hoffnung et al. 2018 (Eur J Clin Microbiol Infect Dis. July; 37(7):1361-1371) discloses a host-protein signature for differentiating between bacterial and viral disease in patients with respiratory infection and fever without source, based on a combining of three blood proteins: tumor necrosis factor-related apoptosis-inducing ligand (TRAIL), interferon gamma induced protein-10 (IP-10), and C-reactive protein (CRP). US 2017/0269081 relates to a method of determining an infection type in a subject comprising measuring the concentration of a first determinant selected from a first group of determinants and a second determinant selected from a second group of determinants in a sample derived from the subject, wherein said concentration is indicative of the infection type. In particular, the publication discloses the identification of expression profiles of multiple determinants measured in blood serum samples, including TRAIL, IP-10 and CRP. Additional disclosures demonstrating the use of various blood biomarkers include, for example, EP 1587955, US 2020/0255898, US 2015/0203899, EP 3221340 and US 2019/0323065.

Urinary biomarkers have been investigated for diagnostic applications, especially to detect or evaluate renal injury or disease. For example, US20150038595 relates to methods and compositions for diagnosis and prognosis of renal injury and renal failure, and Rodriguez-Ortiz et al., (2018, Sci Rep 8(1): 15940) relates to urinary biomarkers for chronic kidney disease. Certain urinary proteins were also evaluated as markers in the context of infective diseases, for example in EP 2711710, Jortani et al. (2004, J Clin Lab Anal.; 18(6): 289-95), Denz et al. (1990, Klin Wochenschr. February 15; 68(4):218-22), Reisinger et al. (2014, PLoS One 9.3), and Whetton et al. (2020, J Proteome Res acs.jproteome.0c00326).

However, despite the need for developing simple and non-invasive diagnostic assays, there is currently no test for differentiating bacterial infections from viral infections based on urinary biomarkers in clinical practice. In particular, the levels of blood proteins, including those proposed as biomarkers for various conditions, do not correlate closely with their levels in urine. This may be attributed to processes such as glomerular filtration, and tubular absorption, in the kidney of adult subjects, responsible for restricting the release of most plasma proteins into the blood.

Early and accurate diagnosis of the infection origin, and in particular, differentiating between bacterial and viral infections, is key for improving patient outcomes and reducing antibiotic resistance. There remains an unmet need for a noninvasive method for rapid and accurate differentiation between viral and bacterial infections.

SUMMARY OF THE INVENTION

The invention provides assays and methods for diagnosing and treating infectious diseases. The invention relates in some embodiments to urinary biomarkers and their use in the differential diagnosis of bacterial and viral infections. The invention further relates to means for determining and providing correct treatment to infection in a non-invasive manner, while minimizing antibiotic misuse.

The invention is based, in part, on the discovery of unique proteomic signatures based on measurements of protein biomarkers in urine, determined to be unexpectedly effective for differentiating between bacterial and viral infections. Surprisingly, as demonstrated herein, diagnostic classifiers were developed, capable of identifying 100% of the subjects afflicted with infections of a bacterial origin. Further, as demonstrated herein, a considerable proportion of the patients afflicted with viral infections could be ruled-out (excluded) from unnecessary antibiotic treatment, while retaining the ability to assign early and adequate antibiotic treatment to all patients with bacterial infections. In contradistinction, other proteins hitherto used or suggested as blood markers, including tumor necrosis factor-related apoptosis-inducing ligand (TRAIL), C-reactive protein (CRP) and CXCL10 (IP-10), were found inappropriate for use as urinary markers, as they were non-delectable in urine (CXCL10, TRAIL) or their urinary levels were not able to differentiate bacterial infections from viral infections (CRP).

Thus, disclosed herein are non-invasive diagnostic assays and methods, useful for differential diagnosis and treatment. In various embodiments, provided are methods and assays for diagnosing an infection, for determining the infection source or etiology, for ruling out a diagnosis of bacterial infection, and for treatment assignment and determination.

According to embodiments of the invention, provided are methods of analyzing a urine sample. In some embodiments, the methods of the invention comprise the step of determining, in a urine sample of a subject, the levels of a plurality of protein markers, e.g. three or more gene products selected from Table 1 below.

TABLE 1

Biomarkers differentiating bacterial and viral infections.

| Gene | Gene product |
|---|---|
| LILRB4 | Leukocyte immunoglobulin-like receptor subfamily B member 4 |
| DPH3 | DPH3 homolog |
| HNRNPM | Heterogeneous nuclear ribonucleoprotein M |
| HIST1H1E | Histone H1.4 |
| PSMD2 | 26S proteasome non-ATPase regulatory subunit 2 |
| PTMA | Prothymosin alpha; Prothymosin alpha, N-terminally processed; Thymosin alpha-1 |
| SELL | L-selectin |
| TRIM28 | Transcription intermediary factor 1-beta |
| SEMG1 | Semenogelin-1; Alpha-inhibin-92; Alpha-inhibin-31; Seminal basic protein |
| ENG | Endoglin |
| CD302 | CD302 antigen |
| STC1 | Stanniocalcin-1 |
| SAA2 | Serum amyloid A-2 protein |
| DSC3 | Desmocollin-3 |

TABLE 1-continued

Biomarkers differentiating bacterial and viral infections.

| Gene | Gene product |
|---|---|
| OPCML | Opioid-binding protein/cell adhesion molecule |
| CRB2 | Protein crumbs homolog 2 |
| EPHB3 | Ephrin type-B receptor 3 |
| CDHR5 | Cadherin-related family member 5 |
| DEFA3; DEFA1 | Neutrophil defensin isoforms - Neutrophil defensin 3; HP 3-56; Neutrophil defensin 2; Neutrophil defensin 1; HP 1-56; Neutrophil defensin 2 |
| IGFALS | Insulin-like growth factor-binding protein complex acid labile subunit |
| F10 | Coagulation factor X; Factor X light chain; Factor X heavy chain; Activated factor Xa heavy chain |
| EPHB2 | Ephrin type-B receptor 2 |
| OGFOD3 | 2-oxoglutarate and iron-dependent oxygenase domain-containing protein 3 |
| CD163 | Scavenger receptor cysteine-rich type 1 protein M130; Soluble CD163 |
| RGAG1 | Retrotransposon gag domain-containing protein 1 |
| GPR116 | Probable G-protein coupled receptor 116 |
| LYPD6B | Ly6/PLAUR domain-containing protein 6B |
| VPS4B | Vacuolar protein sorting-associated protein 4B |
| PDGFRA | Platelet Derived Growth Factor Receptor Alpha |

The levels of said plurality of markers are determined in embodiments of the invention to thereby determine the urinary proteomic signature of the subject (or corresponding sample) with respect to said plurality of markers. The level of each marker may then be compared to reference values, to thereby compare the urinary proteomic signature of said subject (or sample) to urinary proteomic signatures of bacterial, viral and/or healthy control subjects.

In some embodiments, the gene products are selected from the group consisting of LILRB4, PTMA, SEMG1, DPH3, HNRNPM, HIST1H1E, PSMD2, SELL, and TRIM28 gene products. In another embodiment, the gene products may additionally or alternatively be selected from the group consisting of ENG, CD302, STC1, SAA2, DSC3, OPCML, CRB2, EPHB3, CDHR5, DEFA3, DEFA1, IGFALS, F10, EPHB2, OGFOD3, CD163, RGAG1, GPR116, LYPD6B, VPS4B, and PDGFRA. Additional specific combinations of the gene products presented in Table 1 are described in further detail and exemplified hereinbelow.

Thus, in some embodiments, provided are methods for analyzing a urine sample, comprising: determining the levels of at least three gene products selected from Table 1 in the sample, to thereby obtain the urinary proteomic signature of the sample with respect to the at least three gene products, and comparing the level of each gene product to the respective value corresponding to its urinary level during bacterial and/or viral infection, to thereby obtain the urinary proteomic signature of said sample as compared to the urinary proteomic signature of a bacterial and/or viral control, respectively. According to specific embodiments, the analysis may be used for various diagnostic and therapeutic applications, as detailed hereinbelow.

In one aspect, the invention provides a method of determining the infection etiology in a subject suspected of having a bacterial or viral infection, comprising:

a. determining, in a urine sample of the subject, the levels of at least three gene products (polypeptides) selected from Table 1, to thereby obtain the urinary proteomic signature of the subject with respect to the at least three gene products,
b. comparing the level of each gene product to the respective value corresponding to its urinary level during bacterial and/or viral infection, to thereby obtain the urinary proteomic signature of said subject as compared to the urinary proteomic signature of a bacterial and/or viral control, respectively.

In one embodiment, said at least three gene products are selected from the group consisting of: ENG, CD302, STC1, SAA2, DSC3, OPCML, CRB2, EPHB3, CDHR5, DEFA3, DEFA1, IGFALS, F10, EPHB2, OGFOD3, CD163, RGAG1, GPR116, LYPD6B, VPS4B, and PDGFRA gene products. In another embodiment said urinary proteomic signature is determined with respect to ENG, CD302, STC1, SAA2, DSC3, OPCML, CRB2, EPHB3, CDHR5, IGFALS and F10 gene products, and with respect to DEFA3 or DEFA1 gene products. In another embodiment said at least three gene comprise SAA2, PDGFRA, VPS4B, OPCML and ENG gene products. In another embodiment said urinary proteomic signature is determined with respect to SAA2, PDGFRA, VPS4B, OPCML and ENG gene products. Each possibility represents a separate embodiment of the invention.

In another embodiment said at least three gene products are selected from the group consisting of: LILRB4, PTMA, SEMG1, DPH3, HNRNPM, HIST1H1E, PSMD2, SELL, and TRIM28 gene products. In another embodiment said urinary proteomic signature is determined with respect to LILRB4, PTMA, SEMG1, DPH3, HNRNPM, HIST1H1E, PSMD2, SELL, and TRIM28 gene products. Each possibility represents a separate embodiment of the invention.

In another embodiment, said at least three gene products are selected from the group consisting of: ENG, CD302, STC1, SAA2, DSC3, OPCML, CRB2, EPHB3, CDHR5, DEFA3, DEFA1, IGFALS, F10, EPHB2, OGFOD3, CD163, RGAG1, GPR116, LYPD6B, VPS4B, and PDGFRA gene products and the method further comprises determining the levels of at least three additional gene products selected from the group consisting of: LILRB4, PTMA, SEMG1, DPH3, HNRNPM, HIST1H1E, PSMD2, SELL, and TRIM28 gene products in said sample, wherein said urinary proteomic signature is further obtained with respect to the at least three additional gene products. Each possibility represents a separate embodiment of the invention.

In another embodiment of the methods of the invention, the at least three gene products comprise a LILRB4 gene product. In another embodiment, the at least three gene products are LILRB4, PTMA, and SEMG1 gene products. In another embodiment, the at least three gene products are LILRB4, DPH3, and HNRNPM gene products. In another embodiment, said urinary proteomic signature is determined with respect to at least four, at least five, at least, six, at least seven or at least eight of the gene products, wherein each possibility represents a separate embodiment of the invention. In a particular embodiment, said urinary proteomic signature is determined with respect to LILRB4, PTMA, SEMG1, DPH3, HNRNPM, HIST1H1E, PSMD2, SELL, and TRIM28 gene products.

In one embodiment, a urinary proteomic signature substantially different from the urinary proteomic signature of the viral control indicates that the infection etiology is bacterial. In another embodiment, a urinary proteomic signature substantially similar to the urinary proteomic signature of the bacterial control indicates that the infection etiology is bacterial. In another embodiment, a urinary proteomic signature substantially different from the urinary proteomic signature of the viral control and substantially similar to the urinary proteomic signature of the bacterial control indicates that the infection etiology is bacterial. In another embodiment a urinary proteomic signature substantially different from the urinary proteomic signature of the bacterial control indicates that the infection etiology is viral. In another embodiment a urinary proteomic signature substantially similar to the urinary proteomic signature of the viral control indicates that the infection etiology is viral. In another embodiment a urinary proteomic signature substantially different from the urinary proteomic signature of the bacterial control and substantially similar to the urinary proteomic signature of the viral control indicates that the infection etiology is viral. Thus, according to embodiments of the methods of the invention, a urinary proteomic signature substantially different from the urinary proteomic signature of the viral control and/or substantially similar to the urinary proteomic signature of the bacterial control indicates that the infection etiology is bacterial, and a urinary proteomic signature substantially different from the urinary proteomic signature of the bacterial control and/or substantially similar to the urinary proteomic signature of the viral control indicates that the infection etiology is viral.

In yet another embodiment, a urinary proteomic signature comprising significantly enhanced levels of the at least three gene products compared to their respective levels in a bacterial control indicates that the infection etiology is viral. In another embodiment, a urinary proteomic signature comprising significantly reduced levels of the at least three gene products compared to their respective levels in a viral control indicates that the infection etiology is bacterial. In another embodiment, the urinary proteomic signature of said subject is further compared to the urinary proteomic signature of a healthy control subject. Thus, for example, a urinary proteomic signature substantially different from the urinary proteomic signature of the viral control and from the urinary proteomic signature of the healthy control, and substantially similar to the urinary proteomic signature of the bacterial control, indicates that the infection etiology is bacterial. In another example, a urinary proteomic signature substantially different from the urinary proteomic signature of the bacterial control and from the urinary proteomic signature of the healthy control, and substantially similar to the urinary proteomic signature of the viral control indicates that the infection etiology is viral.

In another embodiment of the methods of the invention, the subject is presented with at least two systemic inflammatory response syndrome (SIRS) criteria. In another embodiment, the subject is suspected of having sepsis. In another embodiment, the infection is acute. In another embodiment, the infection is chronic. In another embodiment, the infection is associated with systemic inflammation. In another embodiment, the infection is associated with severe systemic inflammation. In another embodiment, the infection is associated with a condition selected from the group consisting of: Epstein-Barr virus (EBV) infection, cytomegalovirus (CMV) infection, measles, parainfluenza bronchitis, upper respiratory tract infection, lower respiratory tract infection, rash, varicella-zoster virus (VZV) infection, sternitis, peritonitis, pneumonia, rickettsia infection, cellulitis, folliculitis, diverticulitis, colitis, dental infection, bacterial endocarditis, myositis, bacteremia, ascending cholangitis, abscess, bacterial pharyngitis, cholecystitis, empyema, osteomyelitis, parotitis, bronchitis, dengue infection, herpes zoster infection, infectious mononucleosis, influenza, meningitis, and combinations thereof. Each possibility represents a separate embodiment of the invention.

In another embodiment, the method further comprises determining treatment for the subject based on the infection etiology determined. In another embodiment the method further comprises treating the subject with a treatment suitable for the infection etiology determined. In a particular embodiment, the method further comprises treating the subject determined to have an infection of a bacterial etiology with an antibiotic treatment for said infection.

In another embodiment of the methods of the invention, determining the levels of said gene products is performed by an immunoassay. In various embodiments, the immunoassay is selected from the group consisting of dipstick, ELISA (including various multiplexed ELISA technologies), an antibody array, an antibody chip, a lateral flow test, and multiplex bead immunoassay. In another embodiment determining the levels of said gene products is performed by mass spectrometry or using a spectrophotometer.

In another embodiment of the methods of the invention, step b. is performed using a learning and pattern recognition algorithm. For example, the algorithm may include, without limitation, supervised classification algorithms including, but not limited to, gradient boosted trees, random forest, regularized regression, multiple linear regression (MLR), principal component regression (PCR), partial least squares (PLS), discriminant function analysis (DFA) including linear discriminant analysis (LDA), nearest neighbor, artificial neural networks, multi-layer perceptrons (MLP), generalized regression neural network (GRNN), and combinations thereof, or non-supervised clustering algorithms, including, but not limited to, K-means, spectral clustering, hierarchical clustering, gaussian mixture models, and combinations thereof. In a particular embodiment, the algorithm is selected from the group consisting of gradient boosted trees, random forest, regularized regression, and combinations thereof.

In another embodiment of the methods of the invention, step b. comprises comparing the level of each gene product to a predetermined cutoff differentiating between the urinary level of said gene product during bacterial and viral infection. In another embodiment, the respective value corresponding to the urinary level of each gene product during bacterial and/or viral infection is determined from a urine sample of at least one subject diagnosed with the relevant condition (bacterial or viral), from a panel of control samples obtained from a set of subjects diagnosed with said condition, or from a stored set of data from subjects diagnosed with said condition.

Typically, the subject according to the methods of the invention is human. In another embodiment, said subject is at least two years of age. In another embodiment, said subject is an adult human.

In another aspect, there is provided a method of ruling out a bacterial infection in a subject in need thereof, comprising:

a. determining, in a urine sample of the subject, the levels of at least three gene products selected from the group consisting of the gene products listed in Table 1, to thereby obtain the urinary proteomic signature of the subject with respect to the at least three gene products,
b. comparing the level of each gene product to the respective value corresponding to its urinary level during bacterial and/or viral infection, to thereby obtain the urinary proteomic signature of said subject as compared to the urinary proteomic signature of a bacterial and/or viral control, respectively, wherein a urinary proteomic signature substantially different from the urinary proteomic signature of the bacterial control, and/or substantially similar to the urinary proteomic signature of the viral control, indicates that the subject is not afflicted with a bacterial infection.

In one embodiment, the subject is suspected of having a bacterial or viral infection.

In another embodiment, said at least three gene products are selected from the group consisting of ENG, CD302, STC1, SAA2, DSC3, OPCML, CRB2, EPHB3, CDHR5, DEFA3, DEFA1, IGFALS, F10, EPHB2, OGFOD3, CD163, RGAG1, GPR116, LYPD6B, VPS4B, and PDGFRA gene products. In another embodiment, said urinary proteomic signature is determined with respect to ENG, CD302, STC1, SAA2, DSC3, OPCML, CRB2, EPHB3, CDHR5, IGFALS and F10 gene products, and with respect to DEFA3 or DEFA1 gene products. In another embodiment said urinary proteomic signature is determined with respect to LILRB4, PTMA, SEMG1, DPH3, HNRNPM, HIST1H1E, PSMD2, SELL, and TRIM28 gene products. In another embodiment, the method further comprises determining the levels of at least three additional gene products selected from the group consisting of: LILRB4, PTMA, SEMG1, DPH3, HNRNPM, HIST1H1E, PSMD2, SELL, and TRIM28 gene products in said sample, and wherein said urinary proteomic signature is further obtained with respect to the at least three additional gene products.

In another embodiment the infection is associated with a condition selected from the group consisting of: EBV infection, CMV infection, measles, parainfluenza bronchitis, upper respiratory tract infection, lower respiratory tract infection, rash, VZV infection, sternitis, peritonitis, pneumonia, rickettsia infection, insect bite, cellulitis, folliculitis, diverticulitis, colitis, dental infection, bacterial endocarditis, myositis, bacteremia, ascending cholangitis, abscess, bacterial pharyngitis, cholecystitis, empyema, osteomyelitis, parotitis, bronchitis, dengue infection, herpes zoster infection, infectious mononucleosis, influenza, meningitis, and combinations thereof. In another embodiment the infection is acute. In another embodiment the infection is associated with severe systemic inflammation. In another embodiment the subject is presented with at least two SIRS criteria. In another embodiment the subject is suspected of having sepsis. In another embodiment said subject is human. In another embodiment said subject is a human subject over two years of age. In another embodiment said subject is an adult human.

In another embodiment determining the levels of said gene products is performed by an immunoassay. In another embodiment the immunoassay is selected from the group consisting of dipstick, ELISA, an antibody array, an antibody chip, a lateral flow test, and multiplex bead immunoassay. In another embodiment step b. is performed using a learning and pattern recognition algorithm. In another embodiment step b. comprises comparing the level of each gene product to a predetermined cutoff between the urinary level of said gene product during bacterial and viral infection. In another embodiment the respective value corresponding to the urinary level of each gene product during bacterial and/or viral infection is determined from a urine sample of at least one subject diagnosed with the bacterial and/or viral infection, respectively, from a panel of control samples obtained from a set of subjects diagnosed with said bacterial and/or viral infection, or from a stored set of data from subjects diagnosed with said bacterial and/or viral infection.

As disclosed herein, methods according to embodiments of the invention provide for early treatment for infectious disease, as correct diagnosis and treatment assignment (in particular of antibiotic treatment) can be made within hours from symptoms onset, without the need to wait for confirmatory pathogen culture results. For example, a subject presented with signs or symptoms of an infection or a condition as disclosed herein may be tested with assays and methods according to embodiments of the invention that may advantageously provide a prompt answer (e.g. within minutes). Thus, correct treatment assignment may advantageously be provided early during the course of disease (e.g. within 1-4 hours or less than 24 hours of the onset of disease symptoms), before the disease progresses to a more severe and potentially life-threatening stage.

In another aspect, there is provided a method of determining treatment for a subject suspected of having a bacterial or viral infection, comprising:

a. determining, in a urine sample of the subject, the levels of at least three gene products selected from the group consisting of the gene products listed in Table 1, to thereby obtain the urinary proteomic signature of the subject with respect to the at least three gene products,
b. comparing the level of each gene product to the respective value corresponding to its urinary level during bacterial and/or viral infection, to thereby obtain the urinary proteomic signature of said subject as compared to the urinary proteomic signature of a bacterial and/or viral control, respectively, and
c. determining that said subject is amenable for antibiotic treatment if said urinary proteomic signature is substantially different from the urinary proteomic signature of the viral control and/or substantially similar to the urinary proteomic signature of the bacterial control, and determining that said subject is not amenable for antibiotic treatment if said urinary proteomic signature is substantially different from the urinary proteomic signature of the bacterial control and/or substantially similar to the urinary proteomic signature of the viral control.

In another embodiment, the method further comprises determining that said subject is amenable for anti-viral treatment if said urinary proteomic signature is substantially different from the urinary proteomic signature of the bacterial control and/or substantially similar to the urinary proteomic signature of the viral control.

In other embodiment, said antibiotic treatment is selected from the group consisting of broad-spectrum gram-positive antibiotics (e.g. vancomycin, linezolid) broad-spectrum gram-negative antibiotics (e.g. broad-spectrum penicillins such as piperacillin and tazobactam, $3^{rd}$- or $4^{th}$-generation cephalosporins, imipenems, and aminoglycosides), and combinations thereof.

In another embodiment, said at least three gene products are selected from the group consisting of ENG, CD302, STC1, SAA2, DSC3, OPCML, CRB2, EPHB3, CDHR5, DEFA3, DEFA1, IGFALS, F10, EPHB2, OGFOD3, CD163, RGAG1, GPR116, LYPD6B, VPS4B, and PDGFRA gene products. In another embodiment, said urinary proteomic signature is determined with respect to ENG, CD302, STC1, SAA2, DSC3, OPCML, CRB2, EPHB3, CDHR5, IGFALS and F10 gene products, and with respect to DEFA3 or DEFA1 gene products. In another embodiment said urinary proteomic signature is determined with respect to LILRB4, PTMA, SEMG1, DPH3, HNRNPM, HIST1H1E, PSMD2, SELL, and TRIM28 gene products. In another embodiment, the method further comprises determining the levels of at least three additional gene products selected from the group consisting of: LILRB4, PTMA, SEMG1, DPH3, HNRNPM, HIST1H1E, PSMD2, SELL, and TRIM28 gene products in said sample, and wherein said urinary proteomic signature is further obtained with respect to the at least three additional gene products.

In another embodiment the infection is associated with a condition selected from the group consisting of: EBV infection, CMV infection, measles, parainfluenza bronchitis, upper respiratory tract infection, lower respiratory tract infection, rash, VZV infection, sternitis, peritonitis, pneumonia, rickettsia infection, insect bite, cellulitis, folliculitis, diverticulitis, colitis, dental infection, bacterial endocarditis, myositis, bacteremia, ascending cholangitis, abscess, bacterial pharyngitis, cholecystitis, empyema, osteomyelitis, parotitis, bronchitis, dengue infection, herpes zoster infection, infectious mononucleosis, influenza, meningitis, and combinations thereof. In another embodiment the infection is acute. In another embodiment the infection is associated with severe systemic inflammation. In another embodiment the subject is presented with at least two SIRS criteria. In another embodiment the subject is suspected of having sepsis. In another embodiment said subject is human. In another embodiment said subject is a human subject over two years of age. In another embodiment said subject is an adult human.

In another embodiment determining the levels of said gene products is performed by an immunoassay. In another embodiment the immunoassay is selected from the group consisting of dipstick, ELISA, an antibody array, an antibody chip, a lateral flow test, and multiplex bead immunoassay. In another embodiment step b. is performed using a learning and pattern recognition algorithm. In another embodiment step b. comprises comparing the level of each gene product to a predetermined cutoff between the urinary level of said gene product during bacterial and viral infection. In another embodiment the respective value corresponding to the urinary level of each gene product during bacterial and/or viral infection is determined from a urine sample of at least one subject diagnosed with the bacterial and/or viral infection, respectively, from a panel of control samples obtained from a set of subjects diagnosed with said bacterial and/or viral infection, or from a stored set of data from subjects diagnosed with said bacterial and/or viral infection.

In another embodiment, the method further comprises treating said subject amenable for antibiotic and/or anti-viral treatment with the respective treatment, wherein each possibility represents a separate embodiment of the invention. Thus, in another aspect, there is provided a method of treating a subject, comprising administering to a subject determined to be amenable for antibiotic or anti-viral treatment as described herein, the respective antibiotic or anti-viral treatment.

In another aspect, the invention provides an article of manufacture comprising means for specifically detecting and determining the levels of at least three gene products selected from the group consisting of the gene products listed in Table 1 in a urine sample. In one embodiment, the means comprise antibodies specific to LILRB4, PTMA, SEMG1, DPH3, HNRNPM, HIST1H1E, PSMD2, SELL, and TRIM28 gene products. In another embodiment the means comprise antibodies specific to ENG, CD302, STC1, SAA2, DSC3, OPCML, CRB2, EPHB3, CDHR5, IGFALS and F10 gene products, and to DEFA3 or DEFA1 gene products. In various embodiments, the article of manufacture is in the form of a dipstick, an antibody array, an antibody chip, a lateral flow test, or the like.

In another aspect there is provided a diagnostic kit, comprising means for specifically detecting and determining the levels of at least three gene products selected from the group consisting of the gene products listed in Table 1 in a urine sample. In one embodiment, the means comprise antibodies specific to LILRB4, PTMA, SEMG1, DPH3, HNRNPM, HIST1H1E, PSMD2, SELL, and TRIM28 gene products. In another embodiment the means comprise antibodies specific to ENG, CD302, STC1, SAA2, DSC3, OPCML, CRB2, EPHB3, CDHR5, IGFALS and F10 gene products, and to DEFA3 or DEFA1 gene products. In various embodiments the means may be used in various immunoassays including, but not limited to a dipstick, an antibody array, an antibody chip, a lateral flow test, multiplex bead immunoassay, ELISA (including multiplexed ELISA) or other protein staining methods. In another embodiment the kit further comprises a container for collecting the urine sample. In another embodiment said kit further comprises means for comparing the level of each gene product in the sample to the respective value corresponding to its urinary level during bacterial and/or viral infection. In another embodiment said kit further comprises instructions for use, for example instructions for comparing the level of each gene product in the sample to the respective value corresponding to its urinary level during bacterial and/or viral infection, and/or instructions for administering an antibiotic drug to a subject diagnosed as having a bacterial infection using the kit. In another embodiment, the kit further comprises bacterial and/or viral reference controls. In another embodiment, the kit further comprises a suitable treatment, e.g. an antibiotic drug as described herein.

Other objects, features and advantages of the present invention will become clear from the following description and drawings.

DETAILED DESCRIPTION OF THE INVENTION

Figure 1:
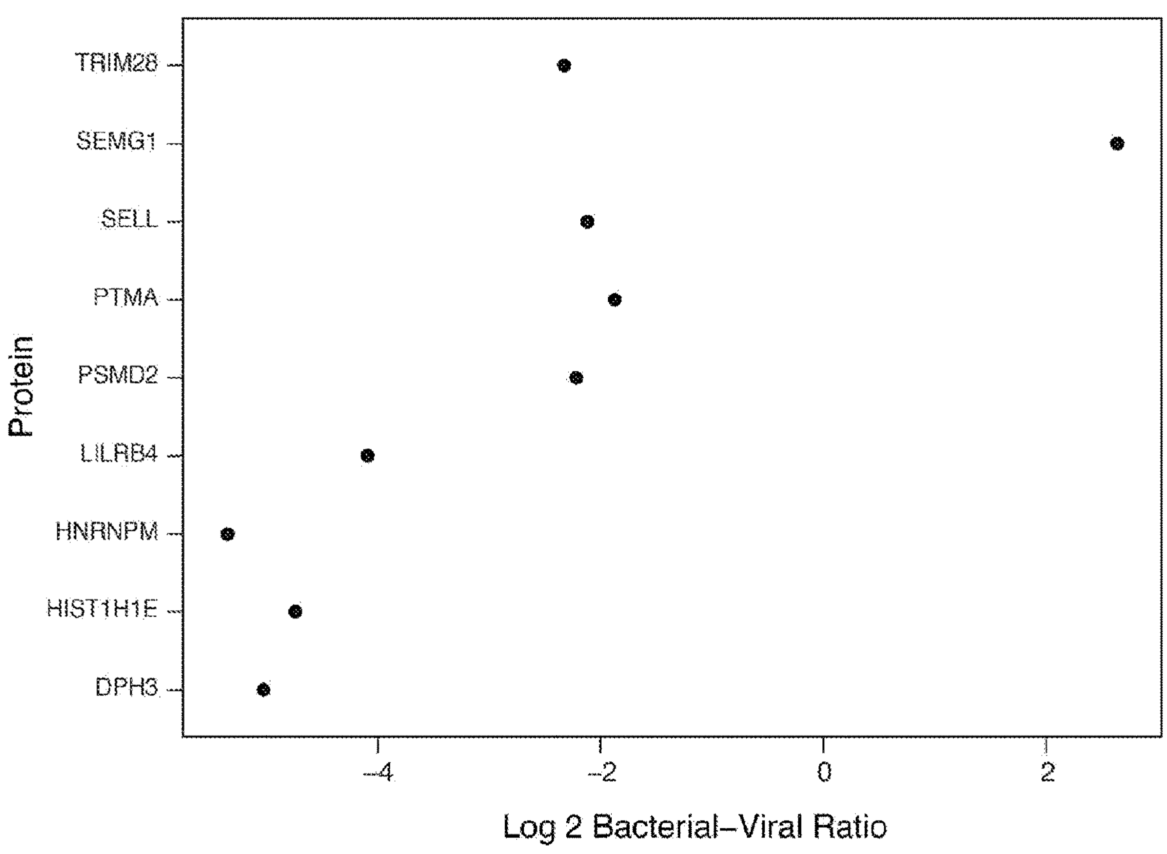
FIG. 1. represents the relative levels of 9 proteins in urine samples of patients with viral and bacterial infections. Results are presented as base 2 logarithm of the bacterial/viral ratio.

The invention provides assays and methods for diagnosing and treating infectious diseases. The invention relates in some embodiments to urinary biomarkers and their use in the differential diagnosis of bacterial and viral infections. The invention further relates to means for determining and providing correct treatment to infection in a non-invasive manner, while minimizing antibiotic misuse. In various embodiments, provided are methods and assays for diagnosing an infection, for determining infection etiology, for ruling out a diagnosis of bacterial infection, for analyzing urine samples, and for treatment assignment and determination.

In one aspect, the invention provides a method of determining the infection etiology in a subject suspected of having a bacterial or viral infection, comprising:

a. determining, in a urine sample of the subject, the levels of at least three gene products selected from the group consisting of the gene products listed in Table 1, to thereby obtain the urinary proteomic signature of the subject with respect to the at least three gene products, and b. comparing the level of each gene product to the respective value corresponding to its urinary level during bacterial and/or viral infection, to thereby obtain the urinary proteomic signature of said subject as compared to the urinary proteomic signature of a bacterial and/or viral control, respectively.

In another aspect, the method of determining the infection etiology in a subject suspected of having a bacterial or viral infection comprises:

a. obtaining a urine sample from the subject, b. determining the levels of at least three gene products, selected from the group consisting of the gene products listed in Table 1, in the sample, to thereby determine the urinary proteomic signature of the subject with respect to the at least three gene products, and c. comparing the level of each gene product to the respective value corresponding to its urinary level during bacterial and/or viral infection, to thereby compare the urinary proteomic signature of said subject to the urinary proteomic signature of a bacterial and/or viral control, respectively.

In another aspect, there is provided a method of ruling out a bacterial infection in a subject in need thereof, comprising:

a. determining, in a urine sample of the subject, the levels of at least three gene products selected from the group consisting of the gene products listed in Table 1, to thereby obtain the urinary proteomic signature of the subject with respect to the at least three gene products, and b. comparing the level of each gene product to the respective value corresponding to its urinary level during bacterial and/or viral infection, to thereby obtain the urinary proteomic signature of said subject as compared to the urinary proteomic signature of a bacterial and/or viral control, respectively, wherein a urinary proteomic signature substantially different from the urinary proteomic signature of the bacterial control, and/or substantially similar to the urinary proteomic signature of the viral control, indicates that the subject is not afflicted with a bacterial infection.

In another aspect, the method of ruling out a bacterial infection in a subject in need thereof comprises:

a. obtaining a urine sample from the subject, b. determining the levels of at least three gene products selected from the group consisting of the gene products listed in Table 1, in the sample, to thereby determine the urinary proteomic signature of the subject with respect to the at least three gene products, and c. comparing the level of each gene product to the respective value corresponding to its urinary level during bacterial and/or viral infection, to thereby compare the urinary proteomic signature of said subject to the urinary proteomic signature of a bacterial and/or viral control, respectively, wherein a urinary proteomic signature substantially different from the urinary proteomic signature of the bacterial control, and/or substantially similar to the urinary proteomic signature of the viral control, indicates that the subject is not afflicted with a bacterial infection.

In another aspect, there is provided a method of determining treatment for a subject suspected of having a bacterial or viral infection, comprising:

a. determining, in a urine sample of the subject, the levels of at least three gene products selected from the group consisting of the gene products listed in Table 1, to thereby obtain the urinary proteomic signature of the subject with respect to the at least three gene products, b. comparing the level of each gene product to the respective value corresponding to its urinary level during bacterial and/or viral infection, to thereby obtain the urinary proteomic signature of said subject as compared to the urinary proteomic signature of a bacterial and/or viral control, respectively, and c. determining that said subject is amenable for antibiotic treatment if said urinary proteomic signature is substantially different from the urinary proteomic signature of the viral control and/or substantially similar to the urinary proteomic signature of the bacterial control, and determining that said subject is not amenable for antibiotic treatment if said urinary proteomic signature is substantially different from the urinary proteomic signature of the bacterial control and/or substantially similar to the urinary proteomic signature of the viral control.

In another aspect, the method of determining treatment for a subject suspected of having a bacterial or viral infection, comprises:

a. obtaining a urine sample from the subject, b. determining the levels of at least three gene products selected from the group consisting of the gene products listed in Table 1, in the sample, to thereby determine the urinary proteomic signature of the subject with respect to the at least three gene products, c. comparing the level of each gene product to the respective value corresponding to its urinary level during bacterial and/or viral infection, to thereby compare the urinary proteomic signature of said subject to the urinary proteomic signature of a bacterial and/or viral control, respectively, and d. determining that said subject is amenable for antibiotic treatment if said urinary proteomic signature is substantially different from the urinary proteomic signature of the viral control and/or substantially similar to the urinary proteomic signature of the bacterial control, and determining that said subject is not amenable for antibiotic treatment if said urinary proteomic signature is substantially different from the urinary proteomic signature of the bacterial control and/or substantially similar to the urinary proteomic signature of the viral control.

In another aspect, there is provided a method of treating a subject suspected of having a bacterial or viral infection, comprising:

a. determining, in a urine sample of the subject, the levels of at least three gene products selected from the group consisting of the gene products listed in Table 1, to thereby obtain the urinary proteomic signature of the subject with respect to the at least three gene products,
b. comparing the level of each gene product to the respective value corresponding to its urinary level during bacterial and/or viral infection, to thereby obtain the urinary proteomic signature of said subject as compared to the urinary proteomic signature of a bacterial and/or viral control, respectively, and
c. treating said subject with antibiotic treatment if said urinary proteomic signature is substantially different from the urinary proteomic signature of the viral control and/or substantially similar to the urinary proteomic signature of the bacterial control.

In another aspect, the method of treating a subject suspected of having a bacterial or viral infection comprises:

a. obtaining a urine sample from the subject,
b. determining the levels of at least three gene products selected from the group consisting of the gene products listed in Table 1, in the sample, to thereby determine the urinary proteomic signature of the subject with respect to the at least three gene products,
c. comparing the level of each gene product to the respective value corresponding to its urinary level during bacterial and/or viral infection, to thereby compare the urinary proteomic signature of said subject to the urinary proteomic signature of a bacterial and/or viral control, respectively, and
d. treating said subject with antibiotic treatment if said urinary proteomic signature is substantially different from the urinary proteomic signature of the viral control and/or substantially similar to the urinary proteomic signature of the bacterial control.

In another aspect, there is provided a method of analyzing a urine sample, comprising:

a. determining the levels of at least three gene products selected from Table 1 in the sample, to thereby obtain the urinary proteomic signature of the sample with respect to the at least three gene products, and
b. comparing the level of each gene product to the respective value corresponding to its urinary level during bacterial and/or viral infection, to thereby obtain the urinary proteomic signature of said sample as compared to the urinary proteomic signature of a bacterial and/or viral control, respectively.

In one embodiment, said at least three gene products are selected from the group consisting of ENG, CD302, STC1, SAA2, DSC3, OPCML, CRB2, EPHB3, CDHR5, DEFA3, DEFA1, IGFALS, F10, EPHB2, OGFOD3, CD163, RGAG1, GPR116, LYPD6B, VPS4B, and PDGFRA gene products. In another embodiment, said urinary proteomic signature is determined with respect to ENG, CD302, STC1, SAA2, DSC3, OPCML, CRB2, EPHB3, CDHR5, IGFALS and F10 gene products, and with respect to DEFA3 or DEFA1 gene products. In another embodiment said urinary proteomic signature is determined with respect to LILRB4, PTMA, SEMG1, DPH3, HNRNPM, HIST1H1E, PSMD2, SELL, and TRIM28 gene products. In another embodiment the method further comprises determining the levels of at least three additional gene products selected from the group consisting of: LILRB4, PTMA, SEMG1, DPH3, HNRNPM, HIST1H1E, PSMD2, SELL, and TRIM28 gene products in said sample, and said urinary proteomic signature is further determined with respect to the at least three additional gene products.

In another embodiment the infection is associated with a condition selected from the group consisting of: EBV infection, CMV infection, measles, parainfluenza bronchitis, upper respiratory tract infection, lower respiratory tract infection, rash, VZV infection, sternitis, peritonitis, pneumonia, rickettsia infection, insect bite, cellulitis, folliculitis, diverticulitis, colitis, dental infection, bacterial endocarditis, myositis, bacteremia, ascending cholangitis, abscess, bacterial pharyngitis, cholecystitis, empyema, osteomyelitis, parotitis, bronchitis, dengue infection, herpes zoster infection, infectious mononucleosis, influenza, meningitis, and combinations thereof. In another embodiment the infection is acute. In another embodiment the infection is associated with severe systemic inflammation. In another embodiment the subject is presented with at least two SIRS criteria. In another embodiment the subject is suspected of having sepsis. In another embodiment said subject is human. In another embodiment said subject is a human subject over two years of age. In another embodiment said subject is an adult human.

In another embodiment determining the levels of said gene products is performed by an immunoassay. In another embodiment the immunoassay is selected from the group consisting of dipstick, ELISA, an antibody array, an antibody chip, a lateral flow test, and multiplex bead immunoassay. In another embodiment comparing the urinary proteomic signatures is performed using a learning and pattern recognition algorithm. In another embodiment comparing the urinary proteomic signatures comprises comparing the level of each gene product to a predetermined cutoff between the urinary level of said gene product during bacterial and viral infection. In another embodiment the respective value corresponding to the urinary level of each gene product during bacterial and/or viral infection is determined from a urine sample of at least one subject diagnosed with the bacterial and/or viral infection, respectively, from a panel of control samples obtained from a set of subjects diagnosed with said bacterial and/or viral infection, or from a stored set of data from subjects diagnosed with said bacterial and/or viral infection.

In another aspect, there is provided an article of manufacture, comprising means for specifically detecting and determining the levels of at least three gene products selected from the group consisting of the gene products listed in Table 1 in a urine sample.

In another aspect, there is provided a diagnostic kit, comprising means for specifically detecting and determining the levels of at least three gene products selected from the group consisting of the gene products listed in Table 1 s in a urine sample, and optionally a container for collecting the urine sample, means for comparing the level of each gene product in the sample to the respective value corresponding to its urinary level during bacterial and/or viral infection, and/or instructions for use in a method of the invention as described herein.

Subjects, Samples and Infections

According to various embodiments of the methods and assays of the invention, a urine sample is obtained from a subject. The subject according to the methods of the invention is typically a human subject. According to some embodiments, the subject is at least two years of age, or in other embodiments an adult human subject. In some embodiments, said subject is suspected of having a bacterial or viral infection. For example, without limitation, said subject may be presented with symptoms or signs of an infection associated with a condition (including, in some embodiments, two or more conditions) selected from the group consisting of: Epstein-Barr virus (EBV) infection, cytomegalovirus (CMV) infection, measles, parainfluenza bronchitis, upper respiratory tract infection (URTI), lower respiratory tract infection, rash, varicella-zoster virus (VZV) infection, sternitis, peritonitis, pneumonia, perianal abscess, rickettsia infection, lung abscess, cellulitis, folliculitis, diverticulitis, colitis, dental infection, bacterial endocarditis, myositis, bacteremia, ascending cholangitis, and combinations thereof, wherein each possibility represents a separate embodiment of the invention. In other embodiments, the condition is selected from the group consisting of bacterial infections associated with abscess (e.g. abdominal abscess, liver abscess, lung abscess), bacterial pharyngitis, cellulitis, cholangitis, cholecystitis, diverticulitis, empyema, gangrenous cholecystitis, osteomyelitis, parotitis, pneumonia, and viral infections associated with asthma exacerbation, bronchitis, CMV, dengue, herpes zoster, infectious mononucleosis, influenza, measles, meningitis, URTI, bronchitis, VZV, and combinations thereof. Each possibility represents a separate embodiment of the invention.

In some embodiments, the subject suspected of having a bacterial or viral infection selected from the group consisting of Epstein-Barr virus (EBV) infection, cytomegalovirus (CMV) infection, measles, parainfluenza bronchitis, upper respiratory tract infection (URTI), lower respiratory tract infection, rash, varicella-zoster virus (VZV) infection, sternitis, peritonitis, pneumonia, rickettsia infection, cellulitis, folliculitis, diverticulitis, colitis, dental infection, bacterial endocarditis, myositis, bacteremia, ascending cholangitis, abscess (e.g. abdominal, liver, lung or perianal abscess), bacterial pharyngitis, cholecystitis, (e.g. gangrenous cholecystitis), empyema, osteomyelitis, parotitis, viral infections associated with asthma exacerbation, bronchitis, dengue infection, herpes zoster infection, infectious mononucleosis, influenza, meningitis, and combinations thereof. In other embodiments, the subject suspected of having a bacterial or viral infection selected from the group consisting of EBV infection, CMV infection, measles, parainfluenza bronchitis, URTI, lower respiratory tract infection, rash, VZV infection, sternitis, peritonitis, pneumonia, rickettsia infection, cellulitis, folliculitis, diverticulitis, colitis, dental infection, bacterial endocarditis, myositis, bacteremia, ascending cholangitis, abscess, bacterial pharyngitis, cholecystitis, empyema, osteomyelitis, parotitis, bronchitis, dengue infection, herpes zoster infection, infectious mononucleosis, influenza, meningitis, and combinations thereof. Each possibility represents a separate embodiment of the invention.

In other embodiments, said subject may have (or is suspected of having) systemic inflammatory response syndrome (SIRS) or sepsis. In other embodiments, said subject may have (oris suspected of having) acute or chronic infection. In other embodiments, said subject may have (or is suspected of having) an infection associated with systemic inflammation. In other embodiments, said subject may have (or is suspected of having) an infection associated with severe systemic inflammation. Each possibility represents a separate embodiment of the invention.

Typically, the subject is not afflicted with a local infection and/or local inflammation.

Generally, SIRS is defined as a condition in which at least two of the following criteria (hereinafter "SIRS criteria") are met:

1. Fever>38° C. or <36° C.,
2. Heart rate>90 beats per minute,
3. Respiratory rate>20 breaths per minute or $PaCO_2$<32 mm Hg, and
4. Abnormal white blood cell count (>12,000/mm$^3$ or <4,000/mm$^3$ or >10% bands).

In sepsis, a documented or presumed infection further accompanies the manifestation of at least two SIRS criteria. In severe sepsis, the aforementioned sepsis criteria are accompanied by associated organ dysfunction, hypoperfusion or hypotension, wherein sepsis-induced hypotension is characterized by the presence of a systolic BP<90 mmHg or a reduction of >40 mmHg from baseline in the absence of other causes of hypotension. Septic shock is a more severe form of sepsis, in which persistent hypotension and perfusion abnormalities are maintained despite adequate fluid resuscitation (which may be further defined as the need for vasopressors to maintain mean arterial pressure>65 mm Hg, and a serum lactate level>18 mg/dL despite adequate volume resuscitation). Finally, multiorgan dysfunction syndrome (MODS) is known as a state of physiological derangements in which organ function is not capable of maintaining homeostasis.

In general, clinical parameters used to evaluate or diagnose medical conditions may be revised or updated from time to time, in an attempt to improve patient management. While the above-mentioned parameters and criteria are currently used to assist in patient management, there remains an unmet need for a noninvasive method for rapid and accurate differentiation between viral and bacterial infections. The principles of the invention provide for rapid and accurate assays and methods that may be used in embodiments of the invention as disclosed herein, regardless of any revisions in clinical criteria that may be employed.

The urine sample to be used in embodiments of the invention is obtained or collected from the subject as is known in the art. Typically, the urine sample is obtained non-invasively, as disclosed herein. In one embodiment, the urine sample is a voided urine sample. In a particular embodiment the sample is collected from the subject without a preceding step of bladder scraping or washing. In another embodiment, the method further comprises the step of freezing the urine sample obtained and thawing the sample prior to the step of determining the levels of the gene products. Conveniently, urine samples may be kept at −20° C. until the analysis is performed. Yet in other embodiments the invention relates to rapid diagnostic and prognostic methods, in which the sample is assayed within hours (e.g. 1-4 hours or less than 24 hours) or minutes (e.g. up to 15, 30 or 45 minutes) of collection. In one embodiment, the sample is a non-sedimented urine sample. In another embodiment, the urine sample is substantially free of residual cells. Each possibility represents a separate embodiment of the invention.

In various embodiments, the methods of the present invention further comprise diluting the urine sample before determining the level of the marker(s). In one embodiment, the sample is diluted in the range of 1:2 to 1:20 for instance, using PBS. In another embodiment, the sample is diluted 1:4, 1:6, 1:8, 1:10, 1:15 or 1:20, e.g. prior to subjecting the sample to an immunoassay. In another embodiment, the urine sample undergoes concentration or filtration. In a preferable embodiment, the sample undergoes ultra-filtration using, for instance, a MILLIPORE Amicon Ultra. As is known in the art, ultra-filtration relates to a variety of membrane filtration in which hydrostatic pressure forces a liquid against a semipermeable membrane. The cut-off of the membrane may be selected from 3KD, 10KD, 30KD or more. In another embodiment, the sample is reconstituted (e.g. with PBS). In another embodiment, following reconstitution, the urine sample is diluted in the range of times 2-times 10 (e.g. prior to subjecting the sample to an immunoassay). In yet other exemplary embodiments (e.g. for analysis using mass spectrometry), the samples may be concentrated by filtration (e.g. using 3 kDa molecular weight cutoff filters) and then subjected to in-solution tryptic digestion, followed by a desalting step. Each possibility represents a separate embodiment of the invention.

In some embodiments, the infection does not involve (or the subject is not concurrently afflicted with), renal injury or disease, e.g. chronic kidney disease. In some embodiments the infection does not include urinary tract infection and/or the subject has not been diagnosed as having urinary tract infection. In other embodiments, the subject is not presented with leukocyturia. In other embodiment the subject is not presented with renal or genitourinary symptoms or signs. In other embodiments the subject is not presented with impaired glomerular filtration or progressive deterioration of glomerular filtration. In other particular embodiments, the subject is not diagnosed with, or suspected of having, tuberculosis or necrotizing enterocolitis. In another particular embodiment, the subject is not diagnosed with, or suspected of having, COVID-19. In yet other embodiments, the subject is afflicted with, or suspected of having, COVID-19. In another embodiment, the subject is not concomitantly afflicted with a non-infective inflammatory disease (e.g. autoimmune disease). Each possibility represents a separate embodiment of the invention.

Antibodies, Assays and Kits

According to various embodiments, the methods and assays of the invention involve detecting or determining the levels of gene products as disclosed herein in urine samples.

In certain embodiments, methods of the invention are performed by an immunoassay, using antibodies specific to gene products of the invention.

An antibody directed (or specific) to an antigen, as used herein is an antibody which is capable of specifically binding the antigen. The term "specifically bind" as used herein means that the binding of an antibody to an antigen probe is not competitively inhibited by the presence of non-related molecules.

It should be understood that when the terms "antibody" or "antibodies" are used, this is intended to include intact antibodies, such as polyclonal antibodies or monoclonal antibodies (mAbs), as well as proteolytic fragments thereof such as the Fab or F(ab')2 fragments. Further included within the scope of the invention are chimeric antibodies; recombinant and engineered antibodies, and fragments thereof.

Exemplary functional antibody fragments comprising whole or essentially whole variable regions of both light and heavy chains are defined as follows:

(i) Fv, defined as a genetically engineered fragment consisting of the variable region of the light chain and the variable region of the heavy chain expressed as two chains;

(ii) single-chain Fv ("scFv"), a genetically engineered single-chain molecule including the variable region of the light chain and the variable region of the heavy chain, linked by a suitable polypeptide linker.

(iii) Fab, a fragment of an antibody molecule containing a monovalent antigen-binding portion of an antibody molecule, obtained by treating whole antibody with the enzyme papain to yield the intact light chain and the Fd fragment of the heavy chain, which consists of the variable and CH1 domains thereof;

(iv) Fab', a fragment of an antibody molecule containing a monovalent antigen-binding portion of an antibody molecule, obtained by treating whole antibody with the enzyme pepsin, followed by reduction (two Fab' fragments are obtained per antibody molecule); and (v) F(ab')2, a fragment of an antibody molecule containing a monovalent antigen-binding portion of an antibody molecule, obtained by treating whole antibody with the enzyme pepsin (i.e., a dimer of Fab' fragments held together by two disulfide bonds).

The term "antigen" as used herein is a molecule or a portion of a molecule capable of being bound by an antibody. The antigen is typically capable of inducing an animal to produce antibody capable of binding to an epitope of that antigen. An antigen may have one or more epitopes. The specific reaction referred to above is meant to indicate that the antigen will react, in a highly selective manner, with its corresponding antibody and not with the multitude of other antibodies which may be evoked by other antigens.

In some embodiments, determining the levels of gene products of the invention in the sample is performed by a process comprising contacting the sample, under conditions such that a specific antigen-antibody complex may be formed, with antibodies directed to the gene products of interest, and quantifying the amount of antigen-antibody complex formed for each gene product, to thereby determine (or obtain) the urinary proteomic signature of the subject with respect to said gene products.

In various embodiments, the immunoassay is selected from the group consisting of dipstick, ELISA (including various multiplexed ELISA technologies), an antibody array, an antibody chip, a lateral flow test, and multiplex bead immunoassay.

In accordance with the principles of the invention, any suitable immunoassay can be used. Such techniques are well known to the ordinarily skilled artisan and have been described in many standard immunology manuals and texts. In certain embodiments, determining the levels of gene products is performed using an antibody array-based method, including, but not limited to an antibody array or an antibody chip. In some embodiments, the array is incubated with an optionally diluted urine sample of the subject so as to allow specific binding between the gene products contained in the sample and the immobilized antibodies, washing out unbound components from the array, incubating the washed array with detectable label-conjugated antibodies of the desired isotype, washing out unbound label from the array, and measuring levels of the label bound to each gene product.

Additional exemplary assays may be based on dipstick technology, as demonstrated, for example, in U.S. Pat. Nos. 4,632,901, 4,313,734 and 4,786,589 5,656,448 and EP 0125118. for example, U.S. Pat. No. 4,632,901, discloses a flow-through type immunoassay device comprising antibody (specific to a target antigen analyte) bound to a porous membrane or filter to which is added a liquid sample. As the liquid flows through the membrane, target analyte binds to the antibody. The addition of sample is followed by addition of labeled antibody. The visual detection of labeled antibody provides an indication of the presence of target antigen analyte in the sample. EP 0125118 discloses a sandwich type dipstick immunoassay in which immunochemical components such as antibodies are bound to a solid phase. The assay device is "dipped" for incubation into a sample suspected of containing unknown antigen analyte. Enzyme-labeled antibody is then added, either simultaneously or after an incubation period. The device next is washed and then inserted into a second solution containing a substrate for the enzyme. The enzyme-label, if present, interacts with the substrate, causing the formation of colored products which either deposit as a precipitate onto the solid phase or produce a visible color change in the substrate solution.

In certain embodiments, the detection of the biomarkers (gene products) may be performed using other immunoassays such as an enzyme-linked immunosorbent assay (ELISA) testing kit. In such assays, for example, samples are typically incubated in the presence of an immobilized first specific binding agent (e.g. an antibody) capable of specifically binding the biomarker. Binding of the biomarker to said first specific binding agent may be measured using any one of a variety of known methods, such as using a labeled second specific binding agent capable of specifically binding the biomarker (at a different epitope) or the first specific binding agent. Exemplary specific binding agents include e.g. monoclonal antibodies, polyclonal antibodies, and antibody fragments such as recombinant antibody fragments, single-chain antibodies (scFv) and the like. In some embodiments, various conventional tags or labels may be used, such as a radioisotope, an enzyme, a chromophore or a fluorophore. A typical radioisotope is iodine$^{-125}$ or sulfur$^{-35}$. Typical enzymes for this purpose include horseradish peroxidase, horseradish galactosidase and alkaline phosphatase.

Alternately, other immunoassays may be used; such techniques are well known to the ordinarily skilled artisan and have been described in many standard immunology manuals and texts. In some embodiments, the methods of the invention are suitable for automated or semi-automated analysis, and may enable clinical, medium or high-throughput screening of multiple samples. For example, automated ELISA systems such as Biotest's Quickstep® ELISA Processor, Maxmat Automated microwell ELISA analyzer (Maxmat S.A., France), or DSX™ Four-Plate System (Dynex Technologies) may conveniently be used, and employed in various methods including, but not limited to multiplexed ELISA methods. Other suitable assays include for example flow cytometry assays (such as singleplex and multiplex bead-based Luminex® assays (Invitrogen), or other multiplex bead immunoassays available in the art.

Lateral flow tests operate on the same principles as ELISA assays as described above. In essence, these tests run the sample along the surface of a pad with reactive molecules that show a visual positive or negative result. The pads are based on a series of capillary beds, such as pieces of porous paper, microstructured polymer, or sintered polymer. Each of these pads has the capacity to transport fluid (e.g., urine) spontaneously. The sample pad acts as a sponge and holds an excess of sample fluid. Once soaked, the fluid flows to the second conjugate pad in which freeze dried bio-active particles called conjugates are stored in a salt-sugar matrix. The conjugate pad contains all the reagents required for an optimized chemical reaction between the target molecule (e.g., a gene product as disclosed herein) and its chemical partner (e.g., antibody) that has been immobilized on the particle's surface. This marks target particles as they pass through the pad and continue across to the test and control lines. The test line shows a signal, often a color. The control line contains affinity ligands which show whether the sample has flowed through and the bio-molecules in the conjugate pad are active. After passing these reaction zones, the fluid enters the final porous material, the wick, that simply acts as a waste container.

In another embodiment determining the levels of said gene products is performed by mass spectrometry or using a micro-spectrometer. For example, mass spectrometry-based, targeted proteomics. For example, using heavy labeled synthetic internal standards for the proteolytic peptides of said gene products. The native peptides and the standards will be measured using a mass spectrometer and the signal from the internal standard is referenced to the native peptides, which represent the original protein in the urine sample. In a non-limitative example, suitable equipment such as the SCIO Near Infrared mini-Spectrometer may be used.

Additional embodiments of the invention are directed to articles of manufacture comprising means for specifically detecting and determining the levels of gene products as disclosed herein in urine samples. In various embodiments, said article of manufacture comprises means for specifically detecting and determining the levels of a gene product set as disclosed herein. In some embodiments, the means the means comprise, consists of, or essentially include, antibodies specific to the gene products of a gene product set as disclosed herein. In some embodiments, the article of manufacture is configured in the form of an immunoassay as disclosed herein, including, but not limited to a dipstick, an antibody array, an antibody chip, or a lateral flow test. In other embodiments, said article of manufacture is amenable for use with an immunoassay as disclosed herein, including, but not limited to a dipstick, an antibody array, an antibody chip, or a lateral flow test.

According to further aspects, the present invention provides kits suitable for use in the methods of the invention. In some embodiments, there is provided a diagnostic kit comprising the article of manufacture. In some embodiments, the kit may further comprise a suitable container or other means for collecting the urine sample. In other embodiments the kit further comprises means for comparing the level of each gene product in the sample to the respective value corresponding to its urinary level during bacterial and/or viral infection. In some embodiments, there is provided a diagnostic kit comprising i) means for collecting a urine sample from a subject and ii) means for determining the level of gene products of the invention in the sample.

In other embodiments, the kit may further contain additional means for determining the level of gene products, including, but not limited to reagents, detectable labels and/or containers which may be used for measuring specific binding of antibodies to the marker antigens of the invention. In other embodiments, the kit may further comprise means for comparing a urinary proteomic signature to control proteomic signatures. In some embodiments the kit contains negative and/or positive control samples. For example, control samples may contain a sample from at least one healthy individual, at least one individual diagnosed with a bacterial infection, or at least one individual diagnosed with a viral infection. In other embodiments, the control samples may include a panel of control samples from a set of healthy individuals or diseased individuals as disclosed herein, or a stored set of data corresponding to control individuals. Optionally, the kits may further comprise means for preparing or processing the sample before measuring the marker levels. In various embodiments, the control samples correspond to subjects diagnosed with an infective condition as disclosed herein. Each possibility represents a separate embodiment of the invention.

In further embodiments the kits further comprise instructions for use, e.g. for using said kits in a diagnostic or analytical method as disclosed herein. In other embodiments, the kit further comprises instructions for assigning treatment or treating a subject according to the methods as disclosed herein. In some embodiments, the kit further comprises a treatment for use on the diagnosed subject, for example at least one antibacterial or antiviral drug as disclosed herein. Each possibility represents a separate embodiment of the invention.

In various embodiments, the invention relates to combinations of gene products, also referred to herein as marker sets, which are detected or quantified in urine samples. In some embodiments, a urinary proteomic signature is determined (or obtained) with respect to a marker set as disclosed herein. In various embodiments, the marker sets include the gene products listed in Table 1 herein, or a subset thereof as disclosed herein. In various embodiments, the marker sets include at least 3 gene products, e.g. 4, 5, 6, 7, 8, 9, 10, 11, 12, or in other embodiments up to about 12, 20, 24 or 29 gene products of those listed in Table 1 herein. In some embodiments, the gene products include, or are selected from the group consisting of, ENG, CD302, STC1, SAA2, DSC3, OPCML, CRB2, EPHB3, CDHR5, DEFA3, DEFA1, IGFALS, F10, EPHB2, OGFOD3, CD163, RGAG1, GPR116, LYPD6B, VPS4B, and PDGFRA gene products. In other embodiments, the gene products include, or are selected from the group consisting of, ENG, CD302, STC1, SAA2, DSC3, OPCML, CRB2, EPHB3 and CDHR5 gene products, and DEFA3 or DEFA1 gene products. In another embodiment, the gene products include, or are selected from the group consisting of, LILRB4, PTMA, SEMG1, DPH3, HNRNPM, HIST1H1E, PSMD2, SELL, and TRIM28 gene products. In another embodiment, the gene products include at least three gene products selected from the group consisting of ENG, CD302, STC1, SAA2, DSC3, OPCML, CRB2, EPHB3, CDHR5, DEFA3, DEFA1, IGFALS, F10, EPHB2, OGFOD3, CD163, RGAG1, GPR116, LYPD6B, VPS4B, and PDGFRA gene products, and at least three gene products selected from the group consisting of LILRB4, PTMA, SEMG1, DPH3, HNRNPM, HIST1H1E, PSMD2, SELL, and TRIM28 gene products. In another embodiment the gene products comprise a LILRB4 gene product. In another embodiment, the gene products are LILRB4, PTMA, and SEMG1 gene products. In another embodiment, the gene products are LILRB4, DPH3, and HNRNPM gene products. In another embodiment the gene products include, or are selected from the group consisting of, SAA2, PDGFRA, VPS4B, OPCML and ENG gene products. In another embodiment, the gene products comprise an SAA2 gene product. In yet another embodiment, the gene products do not comprise an SAA2 gene product. Each possibility represents a separate embodiment of the invention.

In some embodiments, the gene products do not include tumor necrosis factor-related apoptosis-inducing ligand (TRAIL), C-reactive protein (CRP) and/or CXCL10 (IP-10) gene products. In other embodiments, the gene products do not include human neutrophil lipocalin (HNL), sCD14-ST (soluble CD14 antigen subtype; presepsin), urinary trypsin inhibitor (uTi), and/or neopterin. Each possibility represents a separate embodiment of the invention.

In certain embodiments, the gene products of the invention may be found in human urine samples in the form of fragments or peptides, rather than as intact polypeptides (e.g. C-terminally truncated and/or N-terminally truncated fragments). It is to be understood, that the term "gene product" as referred to herein explicitly includes these partial fragments and peptides. In other embodiments, the gene products referred to herein are intact (or substantially intact) polypeptides.

In another embodiment, the markers (gene products) used in connection with the articles of manufacture, kits and assays of the invention comprise, consist of or essentially include a marker set as disclosed herein. Each possibility represents a separate embodiment of the invention.

Diagnostic Applications

According to various embodiments of the methods and assays of the invention, the level of each gene product is compared to the respective value corresponding to its urinary level during bacterial and/or viral infection, to thereby compare the urinary proteomic signature of said subject to the urinary proteomic signature of a bacterial and/or viral control, respectively (or to obtain the urinary proteomic signature of said subject as compared to the urinary proteomic signature of a bacterial and/or viral control, respectively).

In one embodiment, the method is used for differentiating between a bacterial infection and a viral infection in a subject suspected of having a bacterial or viral infection. In another embodiment the method is used for differentially diagnosing an infection in a subject suspected of having a bacterial or viral infection. In another embodiment the method is used for determining the infection etiology in a subject suspected of having a bacterial or viral infection. In another embodiment the method is used for ruling out a bacterial infection in a subject in need thereof. In another embodiment the method is used for determining treatment for a subject suspected of having a bacterial or viral infection.

In some embodiments, a urinary proteomic signature substantially different from the urinary proteomic signature of the viral control and/or substantially similar to the urinary proteomic signature of the bacterial control indicates that the infection etiology is bacterial.

In some embodiments, a urinary proteomic signature substantially different from the urinary proteomic signature of the bacterial control and/or substantially similar to the urinary proteomic signature of the viral control indicates that the infection etiology is viral.

According to embodiments of the invention, substantial difference or similarity of proteomic signatures are determined (or obtained) considering the collective levels of gene products of the signature. In some embodiments, a substantially different urinary proteomic signature compared to a control comprises significantly enhanced levels of a set of gene products as disclosed herein compared to their respective control levels. In other embodiments a substantially different urinary proteomic signature compared to a control comprises significantly reduced levels of a set of gene products as disclosed herein compared to their respective control levels. In yet other embodiments, a substantially different urinary proteomic signature compared to a control comprises both significantly enhanced levels of one or more markers as disclosed herein and significantly reduced levels of one or more additional markers as disclosed herein compared to their respective control levels. Each possibility represents a separate embodiment of the invention. As used herein, "significant enhanced" and "significantly reduced" levels refer to statistically significant enhancement/reduction, respectively.

In some embodiments, comparing proteomic signatures can be performed using suitable classifiers or algorithms, including, but not limited to, learning and pattern recognition algorithms, supervised classifiers, and the like. A significant difference from control levels, such as from a bacterial or viral control as disclosed herein, may typically and conveniently be performed considering the respective values of both negative and positive control groups (e.g. subjects afflicted with bacterial infections and subjects afflicted with viral infections, respectively, when the sample is taken from a subject afflicted with a viral infection). The methods according to embodiments of the invention may include a step of determining the respective level of gene products as disclosed herein in positive and/or negative control samples, or may employ comparison of the values measured in the test sample to the respective predetermined values or stored data. The test sample may thereby be classified as corresponding to (substantially similar to, or not substantially different from) either the positive or negative control group, as disclosed herein. The positive and negative controls referred to herein typically and conveniently represent control sets, such as a panel of control samples from a set of similarly-diagnosed individuals, or a stored set of data obtained from similarly-diagnosed individuals.

Thus, in some embodiments of the methods of the invention, the comparing step is performed using a learning and pattern recognition algorithm as disclosed herein. In a particular embodiment, the algorithm is selected from the group consisting of gradient boosted trees, random forest, regularized regression, and combinations thereof, wherein each possibility represents a separate embodiment of the invention.

In another embodiment of the methods of the invention, the comparing step comprises comparing the level of each gene product to a predetermined cutoff differentiating between the urinary level of said gene product during bacterial and viral infection. In another embodiment, the respective value corresponding to the urinary level of each gene product during bacterial and/or viral infection is determined from a urine sample of at least one subject diagnosed with the relevant condition (bacterial or viral), from a panel of control samples obtained from a set of subjects diagnosed with said condition, or from a stored set of data from subjects diagnosed with said condition.

In some embodiments, the determining and comparing steps comprise determining the presence or absence of each marker in the sample, wherein the urinary proteomic signature reflects said presence or absence of each marker in said sample. According to additional embodiments, comparing the urinary protein signatures further includes comparing the level of each gene product (including the presence or absence of said gene product) to its urinary level during bacterial and/or viral infection in a specific order or hierarchy, to thereby compare the urinary proteomic signature of said subject to the urinary proteomic signature of a bacterial and/or viral control, respectively. For instance, Example 3 herein demonstrates comparison of urinary proteomic signature using decision tree algorithms, in which the markers were considered in a specific order (CDHR5, then SAA2 then ENG), and separated bacterial from viral infections.

In another embodiment, a urinary proteomic signature substantially different from the urinary proteomic signature of the viral control indicates that the infection is bacterial. In another embodiment, a urinary proteomic signature substantially similar to the urinary proteomic signature of the bacterial control indicates that the infection is bacterial. In another embodiment, a urinary proteomic signature substantially different from the urinary proteomic signature of the viral control and substantially similar to the urinary proteomic signature of the bacterial control indicates that the infection is bacterial. In another embodiment a urinary proteomic signature substantially different from the urinary proteomic signature of the bacterial control indicates that the infection is viral. In another embodiment a urinary proteomic signature substantially similar to the urinary proteomic signature of the viral control indicates that the infection is viral. In another embodiment a urinary proteomic signature substantially different from the urinary proteomic signature of the bacterial control and substantially similar to the urinary proteomic signature of the viral control indicates that the infection is viral.

In yet another embodiment, a urinary proteomic signature comprising significantly enhanced levels of the at least three gene products compared to their respective levels in a bacterial control indicates that the infection is viral. In another embodiment, a urinary proteomic signature comprising significantly reduced levels of the at least three gene products compared to their respective levels in a viral control indicates that the infection is bacterial. In another embodiment, the urinary proteomic signature of said subject is further compared to the urinary proteomic signature of a healthy control subject. Thus, for example, a urinary proteomic signature substantially different from the urinary proteomic signature of the viral control and from the urinary proteomic signature of the healthy control, and substantially similar to the urinary proteomic signature of the bacterial control, indicates that the infection is bacterial. In another example, a urinary proteomic signature substantially different from the urinary proteomic signature of the bacterial control and from the urinary proteomic signature of the healthy control, and substantially similar to the urinary proteomic signature of the viral control indicates that the infection is viral.

In other embodiments, a urinary proteomic signature substantially different from the urinary proteomic signature of the viral control and/or substantially similar to the urinary proteomic signature of the bacterial control, indicates that subject is amenable for antibiotic treatment. In other embodiments a urinary proteomic signature substantially different from the urinary proteomic signature of the bacterial control and/or substantially similar to the urinary proteomic signature of the viral control indicates that the subject is not afflicted with a bacterial infection (or not amenable for antibiotic treatment).

In some embodiments, a urinary proteomic signature comprising significantly enhanced levels of a set of gene products as disclosed herein compared to their respective levels in a bacterial control indicates that the subject is not afflicted with a bacterial infection (or not amenable for antibiotic treatment). In other embodiments, significantly reduced levels of a set of gene products as disclosed herein compared to their respective levels in a viral control indicates that said subject is amenable for antibiotic treatment. In other embodiments, a urinary proteomic signature comprising both significantly enhanced levels of a one or more markers as disclosed herein and significantly reduced levels of one or more additional markers as disclosed herein compared to their respective levels in a bacterial control indicates that the subject is not afflicted with a bacterial infection (or not amenable for antibiotic treatment). In other embodiments, a urinary proteomic signature comprising both significantly enhanced levels of a one or more markers as disclosed herein and significantly reduced levels of one or more additional markers as disclosed herein compared to their respective levels in a viral control indicates that said subject is amenable for antibiotic treatment.

According to exemplary embodiments of the methods of the invention, the subject is suspected of having of having a condition selected from the group consisting of: Epstein-Barr virus (EBV) infection, cytomegalovirus (CMV) infection, measles, parainfluenza bronchitis, upper respiratory tract infection (URTI), lower respiratory tract infection, rash, varicella-zoster virus (VZV) infection, sternitis, peritonitis, pneumonia, perianal abscess, rickettsia infection, lung abscess, cellulitis, folliculitis, diverticulitis, colitis, dental infection, bacterial endocarditis, myositis, bacteremia, ascending cholangitis, and combinations thereof, and the gene products include LILRB4, PTMA, SEMG1, DPH3, HNRNPM, HIST1H1E, PSMD2, SELL, and TRIM28 gene products, or a subset thereof as disclosed herein. On other exemplary embodiments of the methods of the invention, the subject is suspected of having a condition selected from the group consisting of: bacterial infections associated with abscess (e.g. abdominal abscess, liver abscess, lung abscess), bacterial pharyngitis, cellulitis, cholangitis, cholecystitis, diverticulitis, empyema, gangrenous cholecystitis, osteomyelitis, parotitis, pneumonia, and viral infections associated with asthma exacerbation, bronchitis, CMV, dengue, herpes zoster, infectious mononucleosis, influenza, measles, meningitis, URTI, bronchitis, VZV, and combinations thereof, and the gene products include ENG, CD302, STC1, SAA2, DSC3, OPCML, CRB2, EPHB3, CDHR5, DEFA3, DEFA1, IGFALS, F10, EPHB2, OGFOD3, CD163, RGAG1, GPR116, LYPD6B, VPS4B, and PDGFRA gene products, or a subset thereof as disclosed herein. Each possibility represents a separate embodiment of the invention.

In various embodiments, the invention relates to methods useful in diagnosis and assessment in cases in which existing assays are lacking, lengthy or otherwise inappropriate or inadvisable. In some embodiments, the infection is characterized in that the infection site is not readily accessible for sampling or is unknown at the time of sample collection. In other embodiments, the infection is characterized in that identifying the infective pathogen by conventional methods (such as culturing or other microbiological laboratory assays) are too lengthy to provide a diagnostic result in a manner that enables timely and correct treatment determination for said subject. The invention in embodiments thereof overcomes these and other challenges as disclosed herein by assaying a urine sample of said subject in a prompt and non-invasive manner. In some embodiments, the methods of the invention for early treatment for infectious disease, as correct diagnosis and treatment assignment (in particular of antibiotic treatment) can be made within hours (e.g. 1-4 hours or less than 24 hours) from symptoms onset. In some embodiments of the methods of the invention, the determining and comparing steps are performed within 15 minutes, 30 minutes, 60 minutes, 1-4 hours, 3-6 hours or up to 24 hours, collectively, wherein each possibility represents a separate embodiment of the invention Data Analysis Advantageously, the methods of the invention can employ the use of learning and pattern recognition analyzers, clustering algorithms and the like, in order to discriminate between the proteomic signature of a sample or subject and control proteomic signatures as disclosed herein. For example, the methods can comprise determining the levels of at least three gene products as disclosed herein in a urine sample, and comparing the resulting urinary proteomic signature to the urinary proteomic signature of a bacterial and/or viral control using such algorithms and/or analyzers.

In certain embodiments, one or more algorithms or computer programs may be used for comparing the amount of each gene product quantified in the urine sample against a predetermined cutoff (or against a number of predetermined cutoffs). Alternatively, one or more instructions for manually performing the necessary steps by a human can be provided.

Algorithms for determining and comparing urinary proteomic signatures include, but are not limited to, supervised classification algorithms including, but not limited to, gradient boosted trees, random forest, regularized regression, multiple linear regression (MLR), principal component regression (PCR), partial least squares (PLS), discriminant function analysis (DFA) including linear discriminant analysis (LDA), nearest neighbor, artificial neural networks, multi-layer perceptrons (MLP), generalized regression neural network (GRNN), and combinations thereof, or non-supervised clustering algorithms, including, but not limited to, K-means, spectral clustering, hierarchical clustering, gaussian mixture models, and combinations thereof. In a particular embodiment, the algorithm is selected from the group consisting of gradient boosted trees, random forest, regularized regression, and combinations thereof.

Many of the algorithms are neural network-based algorithms. A neural network has an input layer, processing layers and an output layer. The information in a neural network is distributed throughout the processing layers. The processing layers are made up of nodes that simulate the neurons by the interconnection to their nodes. Similar to statistical analysis revealing underlying patterns in a collection of data, neural networks locate consistent patterns in a collection of data, based on predetermined criteria.

In other embodiments, principal component analysis is used. Principal component analysis (PCA) involves a mathematical technique that transforms a number of correlated variables into a smaller number of uncorrelated variables. The smaller number of uncorrelated variables is known as principal components. The first principal component or eigenvector accounts for as much of the variability in the data as possible, and each succeeding component accounts for as much of the remaining variability as possible. The main objective of PCA is to reduce the dimensionality of the data set and to identify new underlying variables.

In another embodiment, the algorithm is a classifier. One type of classifier is created by "training" the algorithm with data from the training set and whose performance is evaluated with the test set data. Examples of classifiers used in conjunction with the invention are discriminant analysis, decision tree analysis, receiver operator curves or split and score analysis.

The term "decision tree" refers to a classifier with a flow-chart-like tree structure employed for classification. Decision trees consist of repeated splits of a data set into subsets. Each split consists of a simple rule applied to one variable, e.g., "if value of "variable 1" larger than "threshold 1"; then go left, else go right". Accordingly, the given feature space is partitioned into a set of rectangles with each rectangle assigned to one class.

The terms "test set" or "unknown" or "validation set" refer to a subset of the entire available data set consisting of those entries not included in the training set. Test data is applied to evaluate classifier performance.

The terms "training set" or "known set" or "reference set" refer to a subset of the respective entire available data set. This subset is typically randomly selected, and is solely used for the purpose of classifier construction.

Therapeutic Applications

In some embodiments, the methods of the invention provide for treatment assignment methods and therapeutic methods, comprising e.g. determining treatment for a subject suspected of having a bacterial or viral infection, or determining whether a subject is amenable for a specific treatment as disclosed herein such as an antibiotic treatment and/or an anti-viral treatment. In other embodiments, the methods comprise treating the subject determined to be amenable for said treatment with the treatment in question, for example treating a subject determined to be amenable for antibiotic treatment with said antibiotic treatment. In an exemplary embodiment, the method is used for determining treatment and treating a subject suspected of having a bacterial or viral infection, the method comprising:

a. obtaining a urine sample from the subject,
b. determining the levels of at least three gene products selected from the group consisting of the gene products listed in Table 1, in the sample, to thereby determine the urinary proteomic signature of the subject with respect to the at least three gene products,
c. comparing the level of each gene product to the respective value corresponding to its urinary level during bacterial and/or viral infection, to thereby compare the urinary proteomic signature of said subject to the urinary proteomic signature of a bacterial and/or viral control, respectively,
d. determining that said subject is amenable for antibiotic treatment if said urinary proteomic signature is substantially different from the urinary proteomic signature of the viral control and/or substantially similar to the urinary proteomic signature of the bacterial control, and determining that said subject is not amenable for antibiotic treatment if said urinary proteomic signature is substantially different from the urinary proteomic signature of the bacterial control and/or substantially similar to the urinary proteomic signature of the viral control, and
e. treating said subject determined to be amenable for antibiotic treatment with said antibiotic treatment.

In some embodiments, the antibiotic treatment may include e.g. broad-spectrum gram-positive antibiotics, broad-spectrum gram-negative antibiotics, and combinations thereof. For example, broad-spectrum gram-positive antibiotics may include, without limitation, vancomycin or linezolid. Broad-spectrum gram-negative antibiotics may include, without limitation, broad-spectrum penicillins such as piperacillin and tazobactam, $3^{rd}$- or $4^{th}$-generation cephalosporins, such as cefoperazone, cefotaxime, cefepime and cefpirome, imipenems such as Primaxin (imipenem monohydrate), and aminoglycosides such as gentamicin, tobramycin, amikacin, plazomicin, streptomycin, neomycin, and paromomycin. Each possibility represents a separate embodiment of the invention.

Doses and treatment regimens for disease-specific treatments e.g. as listed above are known in the art and may be determined and adjusted by the skilled artisan (e.g. treating physician) according to the patient's characteristics and disease manifestations.

For example, vancomycin hydrochloride for injection is indicated for the treatment of serious or severe infections caused by susceptible strains of methicillin-resistant (beta-lactam-resistant) staphylococci. Vancomycin hydrochloride is effective in the treatment of staphylococcal infections, including, but not limited to, endocarditis, septicemia, bone infections, lower respiratory tract infections, skin, and skin structure. Vancomycin Hydrochloride for Injection, USP is supplied as a sterile powder in single-dose fliptop vials that contain the vancomycin equivalent of either 500 mg or 1 g. The typical daily intravenous dose for adults is 2 g divided either as 500 mg every six hours or 1 g every 12 hours. Each dose should be administered at no more than 10 mg/min, or over a period of at least 60 minutes, whichever is longer.

In another example, ZYVOX I.V. Injection, ZYVOX Tablets, and ZYVOX for Oral Suspension contain linezolid, which is a synthetic antibacterial agent of the oxazolidinone class. The chemical name for linezolid is (S)—N-((3-(3-Fluoro-4-(4-morpholinyl)phenyl)-2-oxo-5 -oxazolidinyl) methyl)-acetamide. ZYVOX formulations are indicated in the treatment of the following infections caused by susceptible strains of the designated microorganism: vancomycin-resistant *Enterococcus faecium* infections, including cases with concurrent bacteremia, nosocomial pneumonia caused by *Staphylococcus aureus* or *Streptococcus pneumonia*, community-acquired pneumonia caused by *Streptococcus pneumoniae* including cases with concurrent bacteremia, or *Staphylococcus aureus*, and various skin and skin structure infections. Exemplary recommended treatment regimen for adults is 600 mg iv or oral q12h for 10 to 14 days (pneumonia and skin infections) or 14-28 days (vancomycin-resistant *Enterococcus faecium* infections, including concurrent bacteremia).

PIPRACIL, sterile piperacillin sodium, is a semisynthetic broad-spectrum penicillin for parenteral use derived from D(−)-α-aminobenzylpenicillin. The chemical name of piperacillin sodium is sodium (2S,5R,6R)-6-[(R)-2-(4-ethyl-2,3-dioxo-1-piperazinecarboxamido)-2-phenylacetamido]-3,–3-dimethyl-7-oxo-4-thia-1-azabicyclo[3.2.0]heptane-2-carboxylate. PIPRACIL is indicated for the treatment of serious infections caused by susceptible strains of the designated microorganisms in conditions including e.g. Intra-Abdominal Infections including hepatobiliary and surgical infections caused by *E. coli, Pseudomonas aeruginosa*, enterococci, *Clostridium* spp., anaerobic cocci, or *Bacteroides* spp., including *B. fragilis*, Septicemia including bacteremia caused by *E. coli, Klebsiella* spp., *Enterobacter* spp., *Serratia* spp., *P. mirabilis, S. pneumoniae*, enterococci, *P. aeruginosa, Bacteroides* spp., or anaerobic cocci, Lower Respiratory Tract Infections caused by *E. coli, Klebsiella* spp., *Enterobacter* spp., *P. aeruginosa, Serratia* spp., *H. influenzae, Bacteroides* spp., or anaerobic cocci. Skin and Skin Structure Infections caused by *E. coli, Klebsiella* spp., *Serratia* spp., *Acinetobacter* spp., *Enterobacter* spp., *P. aeruginosa, Morganella morganii, Providencia rettgeri, Proteus vulgaris, P. mirabilis, Bacteroides* spp., including *B. fragilis*, anaerobic cocci, or enterococci. Bone and Joint Infections caused by *P. aeruginosa*, enterococci, *Bacteroides* spp., or anaerobic cocci. PIPRACIL may be administered by the intramuscular route (see NOTE) or intravenously as a three- to five-minute intravenous injection or as a 20- to 30-minute infusion. The usual dosage of PIPRACIL for serious infections is 3 to 4 g given every four to six hours as a 20- to 30-minute infusion. For serious infections, the intravenous route should be used.

ZOSYN (piperacillin and tazobactam for injection, USP) is an injectable antibacterial combination product consisting of the semisynthetic antibiotic piperacillin sodium and the β-lactamase inhibitor tazobactam sodium for intravenous administration. ZOSYN is indicated for the treatment of patients with moderate to severe infections caused by piperacillin-resistant, piperacillin/tazobactam-susceptible, β-lactamase producing strains of the designated microorganisms in conditions including e.g. Community-acquired pneumonia (moderate severity only) caused by piperacillin-resistant, β-lactamase producing strains of *Haemophilus influenzae*, and Nosocomial pneumonia (moderate to severe) caused by piperacillin-resistant, β-lactamase producing strains of *Staphylococcus aureus* and by piperacillin/tazobactam-susceptible *Acinetobacter baumanii, Haemophilus influenzae, Klebsiella pneumoniae*, and *Pseudomonas aeruginosa* (Nosocomial pneumonia caused by *P. aeruginosa* should be treated in combination with an aminoglycoside). ZOSYN should be administered by intravenous infusion over 30 minutes. The usual total daily dose of ZOSYN for adults is 3.375 g every six hours totaling 13.5 g (12.0 g piperacillin/1.5 g tazobactam).

The following examples are presented in order to more fully illustrate some embodiments of the invention. They should, in no way be construed, however, as limiting the broad scope of the invention.

EXAMPLES

Example 1. Identification of a Urine Proteomic Signature Differentiating Between Viral and Bacterial Infection

A. Patients and Methods

Patient Characteristics

The study included a total of 76 adult participants, including 56 patients with acute infection, and 20 healthy volunteers as the control group. Of the infected patients, 25 were diagnosed with a bacterial infection, 9 patients had confirmed viral diagnosis, 7 were labeled as indeterminate etiology, and 15 were excluded).

Exclusion criteria included leukocyturia (n=7), diagnosis of urinary tract infection (UTI; n=2), a-febrile patients (n=3) and patients with non-infectious etiology (n=3).

Patients diagnosed with bacterial infection were older and had a higher frequency of dyslipidemia compared to viral patients and controls. The patient cohort was balanced with respect to gender, BMI and prior diagnosis of hypertension.

The patient characteristics are summarized it Table 2 below. The infection etiologies and clinical diagnoses of the patients are listed in Table 3 below, along with a summary of tests by which the diagnoses were confirmed.

TABLE 2

Summary of patient characteristics

| Group | Bacterial infection | Viral infection | Control | p value |
|---|---|---|---|---|
| Patients (n) | 25 | 9 | 20 | |
| Age, years | 66.9 (17.0) | 43.6 (23.7) | 35.3 (9.5) | <0.001 |
| Gender, % male | 60% | 77.8% | 70.0% | 0.577 |
| BMI, kg/m$^2$ | 23.9 (3.2) | 24.7 (3.7) | 22.5 (2.1) | 0.400 |
| Hypertension, % | 56.0% | 33.3% | 0% | <0.001 |
| Dyslipidemia, % | 48.0% | 11.1% | 5% | 0.003 |

TABLE 3

Patient diagnoses

| Count | Diagnosis/Positive test |
|---|---|
| | Bacterial infection |
| 1 | Ascending cholangitis |
| 1 | Abdominal bacterial infections |
| 1 | CT + ERCP + Clinical Dx |

TABLE 3-continued

Patient diagnoses

| Count | Diagnosis/Positive test |
|---|---|
| 1 | Bacteremia |
| 1 | Complicated bacterial infections |
| 1 | Blood culture |
| 1 | Bacteremia + Myositis |
| 1 | Complicated bacterial infections |
| 1 | Blood culture |
| 1 | Bacterial endocarditis |
| 1 | Complicated bacterial infections |
| 1 | Blood culture + Vegetation |
| 2 | Cellulitis |
| 2 | Complicated bacterial infections |
| 2 | Clinical diagnosis |
| 1 | Dental infection |
| 1 | Complicated bacterial infections |
| 1 | History + Dental procedure |
| 1 | Diverticulitis/Colitis |
| 1 | Abdominal bacterial infections |
| 1 | Clinical diagnosis + CT |
| 1 | Deep Vein Thrombosis (DVT) + Cellulitis |
| 1 | Complicated bacterial infections |
| 1 | History + US Doppler |
| 1 | Insect Bite + Cellulitis/folliculitis |
| 1 | Complicated bacterial infections |
| 1 | History |
| 1 | Lung Abscess |
| 1 | Complicated bacterial infections |
| 1 | Chest CT + history |
| 1 | m/p Rickettsia |
| 1 | Community bacterial infections |
| 1 | Clinical diagnosis |
| 1 | m/p infection |
| 1 | Abdominal bacterial infections |
| 1 | Clinical diagnosis |
| 1 | Perianal abscess |
| 1 | Abdominal bacterial infections |
| 1 | CT + Surgery |
| 7 | Pneumonia |
| 7 | Community bacterial infections |
| 1 | Clinical diagnosis + CT |
| 5 | Clinical diagnosis + CXR |
| 1 | CT + Clinical diagnosis |
| 1 | Pneumonia (atypical) |
| 1 | Community bacterial infections |
| 1 | History + CXR |
| 1 | Pneumonia with Emphyema |
| 1 | Community bacterial infections |
| 1 | Pleurocentesis culture |
| 1 | Spontaneous bacterial peritonitis (SBP) |
| 1 | Complicated bacterial infections |
| 1 | Clinical diagnosis + paracentesis |
| 1 | Sternitis |
| 1 | Complicated bacterial infections |
| 1 | Blood culture |
| 25 | Total |
| | Viral infection |
| 3 | Viral EBV/CMV |
| 2 | CMV |
| 2 | Positive Serology |
| 1 | CMV IgM positive |
| 1 | CMV IgM positive with conversion |
| 1 | EBV |
| 1 | Positive Serology |
| 1 | EBV IgM + IgG |
| 2 | Viral Measles |
| 2 | Measles |
| 2 | Serology with seroconversion |
| 1 | Measles with seroconversion |
| 1 | Measles with seroconversion + Urine PCR |
| 3 | Viral Upper Respiratory Tract Infection (URTI)/Lower Respiratory Tract Infection (LTRI)/RASH |
| 1 | m/p Viral infection |
| 1 | Clinical diagnosis |
| 1 | negative for measles |

TABLE 3-continued

| Patient diagnoses | |
|---|---|
| Count | Diagnosis/Positive test |
| 1 | m/p Viral URTI |
| 1 | Clinical diagnosis |
| 1 | Parainfluenza bronchitis |
| 1 | PCR |
| 1 | Parainfluenza type 3 |
| 1 | Viral VZV |
| 1 | VZV (V1) |
| 1 | PCR |
| 1 | VZV positive (smear) |
| 9 | Total |

Sample Preparation

Blood and urine were collected from patients upon hospitalization. Routine chemistry was analyzed immediately, and aliquots of serum and urine were frozen in −80° c. For proteomics analysis, the samples were concentrated using 3 kDa molecular weight cutoff filters and then subjected to in-solution tryptic digestion, followed by a desalting step.

Liquid Chromatography Mass Spectrometry (LC-MS)

The resulting peptides were analyzed using nanoflow liquid chromatography (nanoAcquity) coupled to high resolution, high mass accuracy mass spectrometry (Fusion Lumos). Each sample was analyzed separately in a random order in a discovery mode.

Data Processing

Raw data were processed with MaxQuant v1.6.6.0. The data were searched with the Andromeda search engine against the human proteome database appended with common lab protein contaminants. Quantification was based on the label-free quantification (LFQ) method, based on unique peptides.

Differential Expression analysis was calculated using the limma software package. Missing values were treated based on the majority rules. In a case that one of three replicates was zero, it was treated as Na (i.e. not included in the statistics), if two of three replicates were zero, it was changed to a constant low value (i.e. included in the statistics). False discovery rate (padj) was performed using Benjamini and Hochberg (BH). Significance was based on +/−2-fold change and p.adj<0.05.

B. Results

Proteomic analysis was performed on urine samples of 54 human subjects including subjects diagnosed with bacterial or viral infection (listed in Table 3), and infection-free subjects. Overall, 1307 proteins were detected in the urine samples. Surprisingly, decision tree analysis revealed a signature of only 9 proteins that was sufficient to distinguish patients afflicted with bacterial infection from those afflicted with viral infection. These proteins included host proteins related to immunity or to DNA repair, including human LILRB4, DPH3, HNRNPM, HIST1H1E, PSMD2, PTMA, SELL, TRIM28 and SEMG1 gene products, as set forth in Table 4 below:

TABLE 4

| Details of the 9 protein markers | | |
|---|---|---|
| Accession No. | Gene | Gene product |
| Q8NHJ6 | LILRB4 | Leukocyte immunoglobulin-like receptor subfamily B member 4 |
| Q96FX2 | DPH3 | DPH3 homolog |
| P52272 | HNRNPM | Heterogeneous nuclear ribonucleoprotein M |
| P10412 | HIST1H1E | Histone H1.4 |
| Q13200 | PSMD2 | 26S proteasome non-ATPase regulatory subunit 2 |
| P06454 | PTMA | Prothymosin alpha; Prothymosin alpha, N-terminally processed; Thymosin alpha-1 |
| P14151 | SELL | L-selectin |
| Q13263 | TRIM28 | Transcription intermediary factor 1-beta |
| P04279 | SEMG1 | Semenogelin-1; Alpha-inhibin-92; Alpha-inhibin-31; Seminal basic protein |

For each of the nine proteins selected to compose the proteomic signature, FIG. 1 illustrates the ratio between the average levels in urine samples of the patients afflicted with bacterial or viral infections (represented as log 2 of the bacterial/viral ratio). Table 5 summarizes the results, including the significance (p value following correction for false discovery rate for multiple testing, using the Benjamini-Hochberg procedure), the ratio of biomarker levels (bacterial/viral ratio based on the ratio of geometric means of each group), and the detection rate in bacterial and in viral patients (viral detection represents the proportion of samples in which the protein had a signal).

TABLE 5

Differentiation capacity of the proteins

| Protein | p-value | Bacterial/viral ratio | Bacterial detection | Viral detection |
|---|---|---|---|---|
| LILRB4 | 0.018 | 0.059 | 0.12 | 0.89 |
| DPH3 | 0.031 | 0.031 | 0.04 | 0.67 |
| HNRNPM | 0.031 | 0.024 | 0.12 | 0.78 |
| HIST1H1E | 0.031 | 0.037 | 0.04 | 0.67 |
| PSMD2 | 0.033 | 0.215 | 0.32 | 1.00 |
| PTMA | 0.034 | 0.276 | 1 | 1.00 |
| SELL | 0.034 | 0.231 | 0.56 | 1.00 |
| TRIM28 | 0.046 | 0.200 | 0.28 | 0.89 |
| SEMG1 | 0.046 | 6.236 | 0.28 | 1.00 |

As can be seen in Table 5, 8 of the 9 proteins were detected more frequently in patients with viral infection compared to bacterial infection (viral detections vs. bacterial detections), except for PTMA that was detected in all patients. As can also be seen in Table 5, all proteins selected were detected at significantly higher average levels (4 to 40-fold different) in patients with viral disease compared to patients diagnosed with bacterial disease, with the exception of SEMG1. It is noted that SEMG1 was much more abundant in the viral group as well, with a detection frequency of 100% compared to only 28% in the bacterial infection group. The higher bacterial/viral ratio calculated for SEMG1 resulted from a high value measured in a sample of a single male patient, which might be attributed to residual semen in the sample. The most significant difference between the groups was demonstrated for LILRB4 (p value=0.018), with substantial higher detection frequency in the viral infection group.

Figure 2:
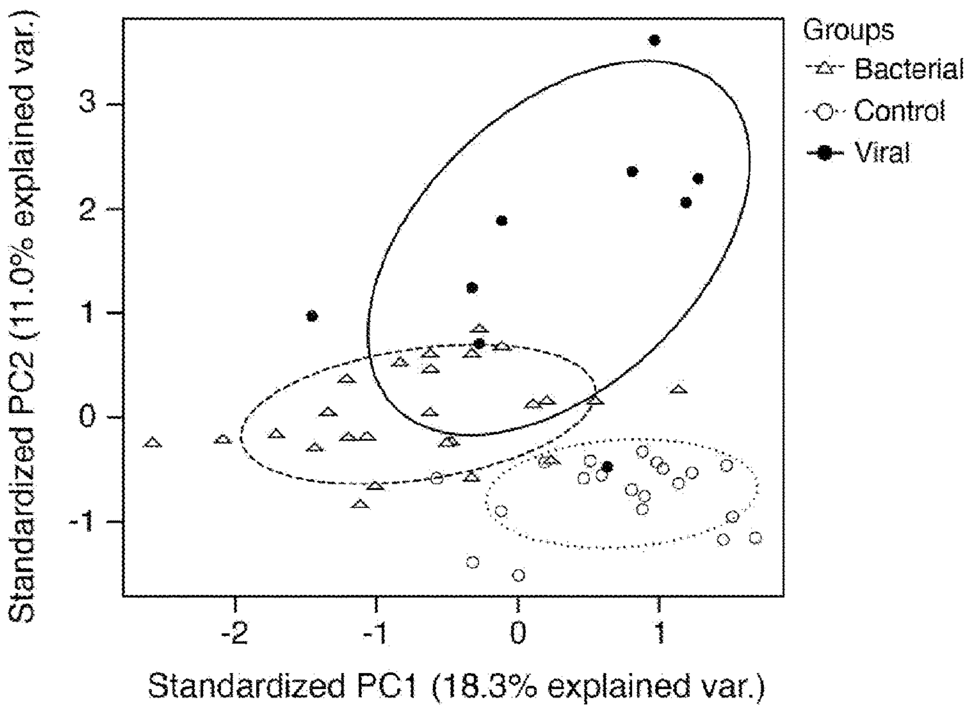
FIG. 2. illustrates principal component analysis (PCA) of linear combinations of urine proteins to discriminate between viral infection, bacterial infection and control group. A clear classification is demonstrated between the three groups.

Example 2. Linear Combination Analysis of Urine Proteins can Differentiate Between Viral, Bacterial and Control Group Next, principal component analysis (PCA) was performed with the urinary biomarkers identified in Example 1 using R's method princomp. As can be seen in FIG. 2, the analysis revealed that linear combinations of urine proteins can differentiate well between the viral, bacterial and control groups.

Figure 3:
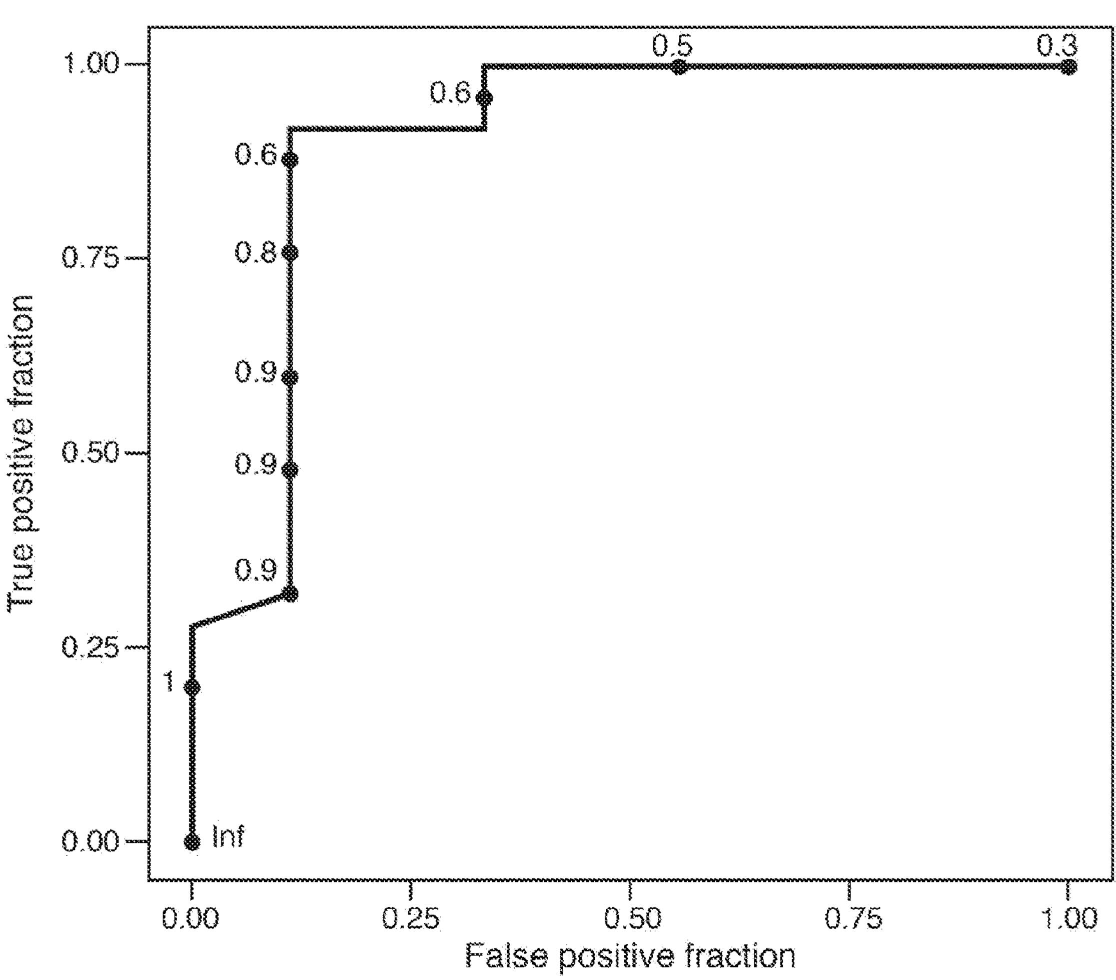
FIG. 3. represents a receiver operating characteristic (ROC) curve of the PCA model, showing the relationship between the true-positive rate (sensitivity) and the false-positive rate (1-specificity) in distinguishing bacterial from viral infections, as described in Example 2.

The discriminative power of the predictive model using the 9-biomarker urinary signature was evaluated by receiver operating characteristic (ROC) curve. The model was done with a leave-one-out cross validation to assess the out-of-sample prediction error. FIG. 3 shows the predicted probability of a bacterial infections presented as fraction of false positive bacterial detections (x-axis) against true positives (y-axis), as a function of the detection threshold. The results demonstrate clinically relevant diagnostic accuracy, wherein 100% sensitivity can be achieved while retaining 30% specificity of the model (FIG. 3) in detecting bacterial infections.

Example 3. Identification of an Additional Urine Proteomic Signature for Differential Diagnosis An additional study was conducted on a second cohort of 380 individuals including healthy human control subjects and patients with various inflammatory and infective conditions. Diagnosis (viral or bacterial infection) was made following data review by 3 or 4 independent physicians. Propensity score method was used to select patients for the proteomic analysis. After best matchings of the groups were made based on age, gender and estimated glomerular filtration (eGFR), subjects in the viral and control groups were 10-16 years younger as compared to those in the bacterial group. Accordingly, 90 samples were prepared and analyzed in discovery mode using mass spectrometry-based proteomics in which the levels of 1,879 proteins were measured essentially as described in Example 1.

The patient characteristics are summarized it Table 6 below. The infection etiologies and clinical diagnoses of the patients are listed in Table 7 below, along with a summary of tests by which the diagnoses were confirmed.

TABLE 6

Summary of patient characteristics

| Parameter | Bacterial | Viral | p value | Control | p value |
|---|---|---|---|---|---|
| n | 32 | 26 | Z | 29 | |
| Age, years (mean ± STD) | 60.0 (17.1) | 49.0 | 0.027 | 43.4 (18.1) | 0.003 |
| Gender, % male | 71.9% | 61.5% | 0.404 | 62.5% | 0.628 |
| Hypertension, % | 53.1% | 30.8% | 0.087 | 6.9% | 0.001 |
| Dyslipidemia, % | 43.8 | 19.2 | 0.048 | 6.9% | 0.003 |
| Diabetes Mellitus, % | 34.4 | 19.2 | 0.199 | 0 | 0.002 |
| Blood CRP, | | | | | |
| admission | 122.1 (111.1) | 22.5 (21.5) | <0.001 | 1.25 (1.9) | <0.001 |
| Urinalysis | 134.4 (94.7) | 26.1 (27.9) | <0.001 | | |
| Max | 168.5 (112.6) | 30.9 (32.8) | <0.001 | | |
| eGFR, ml/min/1.73 m2 | 85.4 (31.3) | 83.2 (19.3) | 0.744 | 95.4 | 0.240 |
| WBCC, $10^9$/L (mean ± STD) | 13.8 (4.9) | 7.3 (2.8) | <0.001 | 6.3 (1.99) | <0.001 |

TABLE 6-continued

| Summary of patient characteristics | | | | | |
|---|---|---|---|---|---|
| Parameter | Bacterial | Viral | p value | Control | p value |
| Neutrophil, % | 79.8 (9.7) | 64.5 (17.7) | <0.001 | 53.5 (13.3) | <0.001 |
| Lymphocyte, % | 10.6 (7.2) | 23.4 (15.1) | <0.001 | 31.2 (8.96) | <0.001 |
| Platelets, $10^9$/L (mean ± STD) | 260.7 (92.9) | 183.9 (51.5) | <0.001 | 212.4 (81.8) | 0.001 |

TABLE 7

| Patient diagnoses in second cohort | |
|---|---|
| Count | Diagnosis/Positive test |
| Bacterial infection | |
| 1 | Abdominal abscess |
| 1 | CT |
| 1 | Abscess (Axillary) |
| 1 | Clinical diagnosis |
| 1 | Abscess gluteal |
| 1 | Clinical diagnosis |
| 1 | Bacterial Pharyngitis |
| 1 | Throat culture |
| 7 | Cellulitis |
| 6 | Clinical diagnosis |
| 1 | Clinical diagnosis + Culture |
| 1 | Cellulitis + Infected hematoma |
| 1 | Clinical diagnosis |
| 1 | Cholangitis |
| 1 | Clinical diagnosis + Culture |
| 2 | Cholecystitis |
| 2 | Clinical diagnosis + Culture |
| 1 | Diverticulitis |
| 1 | Clinical diagnosis |
| 1 | Empyema |
| 1 | Pleurocentesis |
| 1 | Gangrenous cholecystitis |
| 1 | Clinical diagnosis + CT + pathology |
| 1 | Liver abscess |
| 1 | Clinical diagnosis + Culture |
| 1 | Lung Abscess |
| 1 | Osteomyelitis |
| 1 | Clinical diagnosis + wound culture + X-ray |
| 1 | Parotitis |
| 1 | Clinical diagnosis + Culture |
| 7 | Pneumonia |
| 1 | Clinical + CXR + CT |
| 1 | Clinical diagnosis + CT |
| 5 | Clinical diagnosis + CXR |
| 29 | Sum |
| Viral Infection | |
| 1 | Asthma exacerbation |
| 1 | Clinical diagnosis |
| 1 | Bronchitis |
| 1 | Clinical diagnosis |
| 3 | CMV |
| 2 | Positive serology |
| 1 | Serology with Seroconversion |
| 1 | Dengue |
| 1 | Serology |
| 1 | Fever + headache |
| 1 | Clinical diagnosis |
| 3 | Gastroenteritis |
| 3 | Clinical diagnosis |
| 1 | Herpes Zoster V1-2 |
| 1 | Clinical diagnosis |
| 1 | Infectious mononucleosis |
| 1 | Serology |
| 3 | Influenza |
| 3 | Clinical diagnosis + PCR |
| 4 | Influenza A |
| 3 | Clinical diagnosis + PCR |
| 1 | PCR |

TABLE 7-continued

| Patient diagnoses in second cohort | |
|---|---|
| Count | Diagnosis/Positive test |
| 1 | Measles |
| 1 | Clinical diagnosis + serology |
| 1 | Meningitis Aseptic |
| 1 | Clinical diagnosis + CSF PCR |
| 2 | URTI |
| 2 | Clinical diagnosis |
| 2 | Viral Bronchitis |
| 1 | Clinical diagnosis + PCR |
| 1 | PCR |
| 1 | Viral infection |
| 1 | Clinical diagnosis |
| 1 | Viral meningitis |
| 1 | PCR |
| 2 | VZV |
| 1 | Clinical diagnosis |
| 1 | Clinical diagnosis + PCR |
| 1 | VZV |
| 1 | PCR |
| 30 | Sum |

For the analysis the Lasso algorithm was used, as implemented in the R package glmnet, with L-1 penalty (alpha=1). The shrinkage parameter (lambda) was selected using cross-validation.

Based on the proportions of samples in each group that had detectable levels of each protein, gene products in which the difference in detection proportions was the most significant (after filtering proteins with less than 3 peptides in the LC-MS) were selected for further analysis. These proteins are listed in Table 8 below, along with the proportion of samples of each group in which the gene product in question was identified. The ratio between the average levels in urine samples of the patients afflicted with bacterial or viral infections (represented as log 2 of the bacterial/viral ratio) is also shown for the 12 best-performing markers.

TABLE 8

| Differentiation capacity of the proteins | | | | | |
|---|---|---|---|---|---|
| Protein | Pval | Bacterial | Viral | Control | Ratio |
| ENG | 0.000241 | 0.344828 | 0.857143 | 0.90625 | 0.3895 |
| CD302 | 0.0003 | 0.551724 | 0.071429 | 0.03125 | 12.1878 |
| STC1 | 0.000738 | 0.344828 | 0.821429 | 0.8125 | 0.4333 |
| SAA2 | 0.00081 | 0.827586 | 0.357143 | 0.125 | 125.3296 |
| DSC3 | 0.00126 | 0.103448 | 0.535714 | 0.90625 | 0.2748 |
| OPCML | 0.001401 | 0.413793 | 0.857143 | 0.9375 | 0.4129 |
| CRB2 | 0.002181 | 0.206897 | 0.642857 | 0.78125 | 0.4891 |
| EPHB3 | 0.002311 | 0.241379 | 0.678571 | 0.8125 | 0.4884 |
| CDHR5 | 0.002327 | 0.482759 | 0.892857 | 0.96875 | 0.2628 |
| DEFA3; DEFA1 | 0.003039 | 1 | 0.678571 | 1 | 0.8440 |
| IGFALS | 0.003117 | 0.448276 | 0.857143 | 0.9375 | 0.2421 |
| F10 | 0.003398 | 0.448276 | 0.071429 | 0.03125 | 38.7266 |
| EPHB2 | 0.003874 | 0.413793 | 0.821429 | 0.875 | |

TABLE 8-continued

| Differentiation capacity of the proteins | | | | | |
|---|---|---|---|---|---|
| Protein | Pval | Bacterial | Viral | Control | Ratio |
| OGFOD3 | 0.004385 | 0.689655 | 1 | 0.90625 | |
| CD163 | 0.004967 | 0.206897 | 0.607143 | 0.59375 | |
| RGAG1 | 0.004967 | 0.206897 | 0.607143 | 0.5 | |
| GPR116 | 0.005041 | 0.344828 | 0.75 | 0.9375 | |
| LYPD6B | 0.005041 | 0.344828 | 0.75 | 0.78125 | |
| VPS4B | 0.005324 | 0.241379 | 0.642857 | 0.78125 | |
| PDGFRA | 0.005324 | 0.241379 | 0.642857 | 0.84375 | |

Using shrinkage methods as described above, a urinary proteomic signature of 12 host proteins was created, distinguishing patients afflicted with bacterial infection from those afflicted with viral infection (AUC=0.7635). The details of these gene products are provided in Table 9 below.

Figure 4:
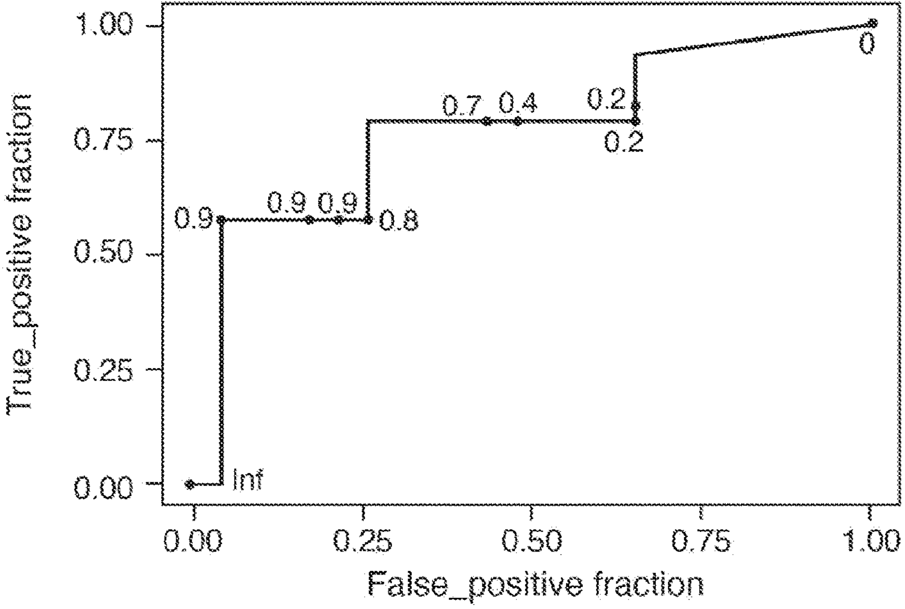
FIG. 4. presents a ROC curve showing the relationship between the true-positive rate (sensitivity) and the false-positive rate (1-specificity) in distinguishing bacterial from viral infections, as described in Example 3.

FIG. 4 illustrates a receiver operating characteristic (ROC) curve, showing true positive and false positive discrimination analysis of bacterial infection. As can be seen in FIG. 4, about 50% of bacterial patients can be detected with 10% false positive results, wherein 100% sensitivity can be achieved while retaining 30% specificity.

TABLE 9

| Details of the 12 protein markers | | |
|---|---|---|
| Accession No. | Gene | Gene product |
| P17813 | ENG | Endoglin |
| Q8IX05 | CD302 | CD302 antigen |
| P52823 | STC1 | Stanniocalcin-1 |
| P0DJI9 | SAA2 | Serum amyloid A-2 protein |
| Q14574 | DSC3 | Desmocollin-3 |
| Q14982 | OPCML | Opioid-binding protein/cell adhesion molecule |
| Q5IJ48 | CRB2 | Protein crumbs homolog 2 |
| P54753 | EPHB3 | Ephrin type-B receptor 3 |
| Q9HBB8 | CDHR5 | Cadherin-related family member 5 |
| P59666; P59665 | DEFA3; DEFA1 | Neutrophil defensin isoforms - Neutrophil defensin 3; HP 3-56; Neutrophil defensin 2; Neutrophil defensin 1; HP 1-56; Neutrophil defensin 2 |
| P35858 | IGFALS | Insulin-like growth factor-binding protein complex acid labile subunit |
| P00742 | F10 | Coagulation factor X; Factor X light chain; Factor X heavy chain; Activated factor Xa heavy chain |

Figure 5:
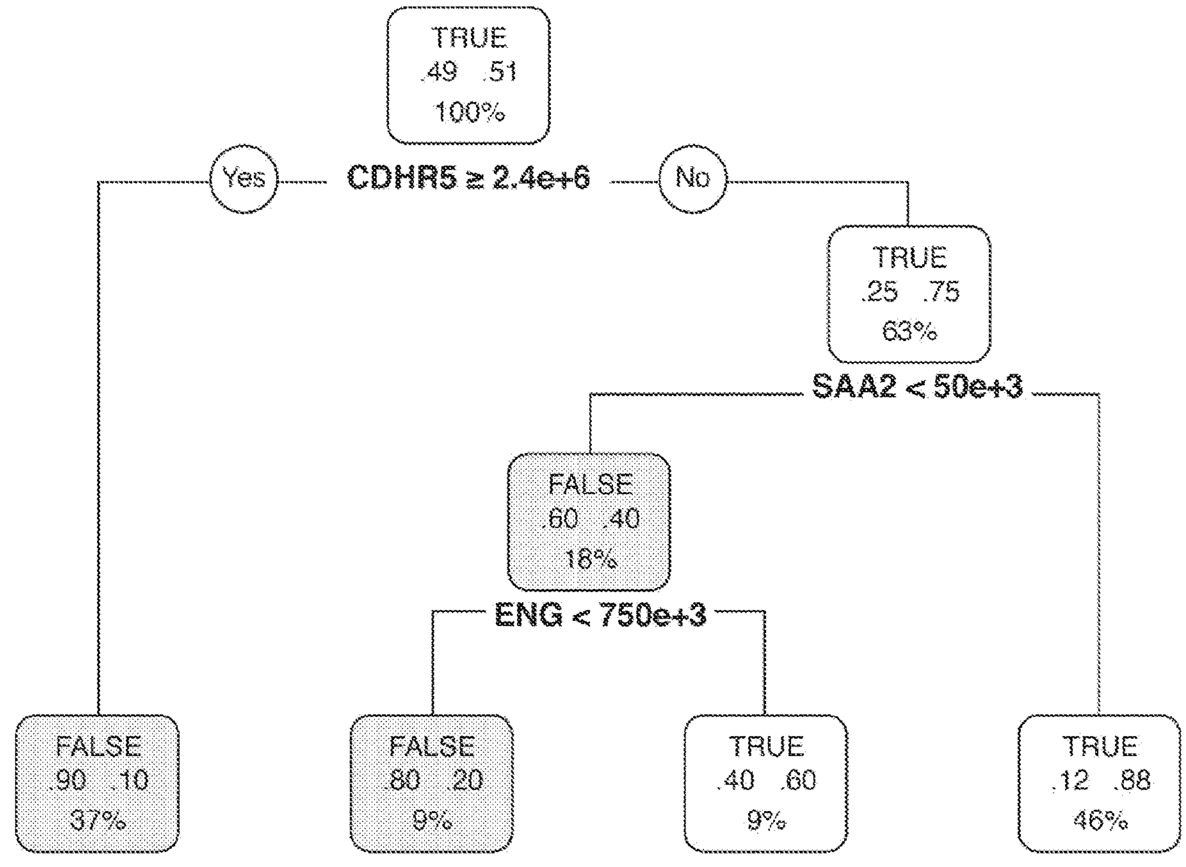
FIG. 5. shows an exemplary decision tree analysis for bacterial infections.

FIG. 5 shows an exemplary decision tree analysis for bacterial infections using a subset of three markers of the gene products listed in Table 9, considered in the order: CDHR5, then SAA2 then ENG. In FIG. 5, each split in the decision tree represents a decision criterion as set forth in the legend below each node. The color of each node represents the ratio of viral to bacterial patients falling in this criterion, going from gray (viral) to white (bacterial). The two decimal numbers represent the proportion of viral infections or bacterial infections, respectively, of the overall population in the node, and the bottom number represents the proportion of the overall population included in this node.

Figure 6:
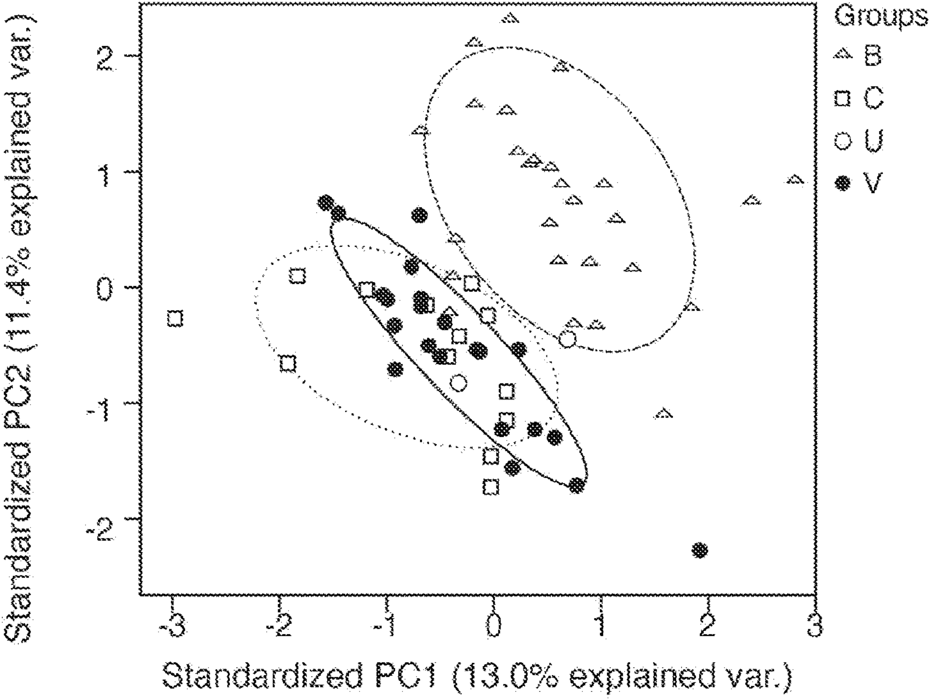
FIG. 6. shows a PCA analysis based on the 12 gene products as described in Example 3. B— bacterial; C— healthy control; U— undetermined; V— viral.

PCA analysis (FIG. 6) shows that the 12 gene products listed in Table 9 provide clear identification of bacterial infections which are highly differentiated from the remaining groups.

Further analysis by shrinkage regression revealed that a combination of only 5 of the 12 proteins of Table 9 was still sufficient to provide discrimination. These selected gene products are listed in Table 10 below.

TABLE 10

| Five-marker signature details | | |
|---|---|---|
| Gene | Accession No. | Gene product |
| SAA2 | P0DJI9 | Serum amyloid A-2 protein |
| PDGFRA | P16234 | Platelet Derived Growth Factor Receptor Alpha |
| VPS4B | VPS4B | Vacuolar protein sorting-associated protein 4B |
| OPCML | Q14982 | Opioid-binding protein/cell adhesion molecule |
| ENG | P17813 | Endoglin |

Example 4. Known Blood Markers are not Identified in Urine

The levels of TRAIL, CXCL10 (IP-10) and CRP were further measured in urine samples of healthy subjects and subjects afflicted with various infections, essentially as described in Example 3. The targeted proteomic experiment was performed on a total of 91 samples: 32 healthy controls, 30 samples obtained from subjects with viral infections, and 29 samples obtained from subjects with bacterial infections.

In striking contradistinction from the markers identified in Examples 1-3 herein, TRAIL and CXCL10 gene products were both undetectable in any of the urine samples.

As to CRP, gene products corresponding to CRP were detected in the urine samples as follows: 14 out of the 32 control samples (43.8%), 26 out of the 30 viral samples (86.7%) and 28 out of the 29 bacterial samples (96.6%) contained a CRP gene product. However, while the increased abundance of urinary CRP in infected patients compared to healthy subjects reached statistical significance (Chi square<0.001), no statistical significance was reached when comparing subjects with viral infections to those with bacterial infections (Chi square p=0.173).

Further, even when comparing the levels of urinary CRP in the three groups, which were different between infected patients and healthy controls (median IQR in controls: 0 [0-1,771,063], in viral infections: 6,191,530 [1,742,375-14, 390,560] and in bacterial infections 15,081,115 [2,886,969-47,985,575], p<0.001, Kruskal-Wallis H test), the difference between viral and bacterial patients did not remain significant following correction for multiple comparisons (p=0.011, Mann-Whitney Test for comparison between viral and controls).

DISCUSSION

The results presented in the Examples hereinabove demonstrate the identification of unique proteomic signatures in urine samples, providing for non-invasive diagnosis of infectious diseases as being of bacterial or viral origin, irrespective of the specific pathology or infecting pathogen. As demonstrated herein, correct differential diagnosis can be obtained, distinguishing patients with bacterial infections from those afflicted with viral infections as well as from control subjects, rather than merely separating healthy subjects from individuals afflicted with inflammation or infectious disease. In addition, it is demonstrated herein that the differential diagnosis needs not be limited to subjects in which the existence of an infection has already been confirmed.

Further, it is demonstrated herein that a reliable, clinically relevant diagnostic assay can be provided based on a classifier of urine-borne host proteins. Advantageously, the assays disclosed herein provide for detection of all bacterial infection, thereby ensuring adequate and timely antibiotic treatment to all patients in need thereof, while sparing hospital visits and unnecessary antibiotic treatment from 30% of the patients afflicted with viral infections, thereby providing a remarkable contribution to currently applied diagnostic procedures.

These results are even more surprising in view of the results presented in Example 4 herein, exemplifying the lack of correlation that is typically observed between blood proteins and their urinary levels, including those hitherto suggested or recognized as diagnostic biomarkers when measured in blood. In particular, as demonstrated herein, blood proteins can be completely undetectable in urine samples, or can be present at relative amounts or abundance incompatible with their use for diagnostic applications, such as for differentiation between bacterial and viral infections. In contradistinction, detectable and consistent levels compatible with use as urinary biomarkers were unexpectedly characteristic of the selected gene products and diagnostic signatures of the invention.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The invention claimed is:

1. A method for treating a subject suffering from an infection, the method comprising:

determining whether the subject has a bacterial infection by performing an immunoassay on a urine sample obtained from the subject to determine if the urine sample has detect a presence of at least two peptide fragments comprising a peptide fragment of C-reactive protein (CRP) and a peptide fragment of SAA2 and not comprising a peptide fragment of tumor necrosis factor-related apoptosis-inducing ligand (TRAIL), wherein the immunoassay comprises subjecting the urine sample to antibodies specific to the at least two peptide fragments, to thereby construe a urinary proteomic signature of the subject;

wherein the subject is administered with an antibiotic drug if the urinary proteomic signature of the subject corresponds to a bacterial control urinary proteomic signature of a subject suffering from the bacterial infection; and wherein the subject is not administered with an antibiotic drug if the urinary proteomic signature of the subject corresponds to a viral control urinary proteomic signature of a subject suffering from a viral infection.

2. The method of claim 1, wherein the bacterial control proteomic signature and the viral control proteomic signature are obtained from mass-spec analysis of urine samples obtained from a plurality of subjects suffering from a bacterial and viral infections respectively.

3. The method of claim 1, wherein, the immunoassay is a lateral flow test.

4. The method of claim 1, wherein performing the immunoassay comprises determining a level of each of the at least two peptide fragments in the urine sample.

5. The method of claim 4, further comprising comparing the determined level of each of the at least two peptide fragments to a predetermined cutoff value.

6. The method of claim 1, wherein the at least two peptide fragments further comprise at least one fragment of the gene products selected from the group consisting of ENG, CD302, STC1, DSC3, OPCML, CRB2, EPHB3, CDHR5, DEFA3, DEFA1, IGFALS, F10, EPHB2, OGFOD3, CD163, RGAG1, GPR116, LYPD6B, VPS4B, and PDGFRA.

7. The method of claim 1, wherein the at least two peptide fragments are fragments of the gene products selected from the group consisting of LILRB4, PTMA, SEMG1, DPH3, HNRNPM, fflSTIHIE, PSMD2, SELL, and TRIM28 peptide fragments.

8. The method of claim 1, wherein the subject is presenting at least two systemic inflammatory response syndrome (SIRS) criteria.

9. The method of claim 1, wherein the infection is associated with a condition selected from the group consisting of: Epstein-Barr virus (EBV) infection, cytomegalovirus (CMV) infection, measles, parainfluenza bronchitis, upper respiratory tract infection, lower respiratory tract infection, rash, varicella-zoster virus (VZV) infection, stemitis, peritonitis, pneumonia, rickettsia infection, insect bite, cellulitis, folliculitis, diverticulitis, colitis, dental infection, bacterial endocarditis, myositis, bacteremia, ascending cholangitis, abscess, bacterial pharyngitis, cholecystitis, empyema, osteomyelitis, parotitis, bronchitis, dengue infection, herpes zoster infection, infectious mononucleosis, influenza, meningitis, and combinations thereof.

10. The method of claim 1, wherein the antibiotic drug is selected from the group consisting of broad-spectrum gram-positive antibiotics, broad-spectrum gram-negative antibiotics, and combinations thereof.

* * * * *